United States Patent
Izumi et al.

(10) Patent No.: US 11,730,171 B2
(45) Date of Patent: Aug. 22, 2023

(54) COMPOSITION FOR ENHANCING BREAST MILK COMPONENT

(71) Applicant: MORINAGA MILK INDUSTRY CO., LTD., Tokyo (JP)

(72) Inventors: Hirohisa Izumi, Kanagawa (JP); Tatsuya Ehara, Kanagawa (JP); Akari Hiraku, Kanagawa (JP); Mai Murata, Kanagawa (JP); Noriyuki Iwabuchi, Kanagawa (JP)

(73) Assignee: Morinaga Milk Industry Co., Ltd., Tokyo (JP)

(*) Notice: Subject to any disclaimer, the term of this patent is extended or adjusted under 35 U.S.C. 154(b) by 262 days.

(21) Appl. No.: 16/982,351

(22) PCT Filed: Mar. 25, 2019

(86) PCT No.: PCT/JP2019/012602
§ 371 (c)(1),
(2) Date: Sep. 18, 2020

(87) PCT Pub. No.: WO2019/182160
PCT Pub. Date: Sep. 26, 2019

(65) Prior Publication Data
US 2021/0106017 A1    Apr. 15, 2021

(30) Foreign Application Priority Data

Mar. 23, 2018 (JP) .................... 2018-056597

(51) Int. Cl.
A61K 35/745    (2015.01)
A23C 9/152    (2006.01)
A23L 33/135    (2016.01)
A61K 38/21    (2006.01)

(52) U.S. Cl.
CPC ............ *A23C 9/152* (2013.01); *A23L 33/135* (2016.08); *A61K 35/745* (2013.01); *A61K 38/21* (2013.01)

(58) Field of Classification Search
CPC .................................................. A61K 35/745
See application file for complete search history.

(56) References Cited

U.S. PATENT DOCUMENTS

| | | |
|---|---|---|
| 2010/0266550 A1 | 10/2010 | Martin Jimenez et al. |
| 2012/0093874 A1 | 4/2012 | Ochiya et al. |
| 2013/0280368 A1 | 10/2013 | Izumi et al. |

FOREIGN PATENT DOCUMENTS

| | | |
|---|---|---|
| EP | 2127661 A1 | 12/2009 |
| JP | 2007-169200 A | 7/2007 |
| JP | 2010-528093 A | 8/2010 |
| JP | 2013-245174 A | 12/2013 |

(Continued)

OTHER PUBLICATIONS

Extended European Search Report for European Patent App. No. 19771941.2 (dated Oct. 20, 2021).

(Continued)

*Primary Examiner* — Rosanne Kosson
(74) *Attorney, Agent, or Firm* — Cermak Nakajima & McGowan LLP; Shelly Guest Cermak

(57) ABSTRACT

Provided is a composition that may be used for a specific use application, such as a composition for enhancing a breast milk component. A composition containing a bacterium of the genus *Bifidobacterium* as an active ingredient is described.

7 Claims, 1 Drawing Sheet

(56) References Cited

FOREIGN PATENT DOCUMENTS

| WO | WO2011/007815 A1 | 1/2011 | |
|---|---|---|---|
| WO | WO2012/096272 A1 | 7/2012 | |
| WO | WO2015/090349 A1 | 6/2015 | |
| WO | WO-2015086789 A1 * | 6/2015 | ............... A23C 9/20 |
| WO | WO-2019068356 A1 * | 4/2019 | ............... A23C 9/20 |

OTHER PUBLICATIONS

Enomoto, T., et al., "Effects of Bifidobacterial Supplementation to Pregnant Women and Infants in the Prevention of Allergy Development in Infants and on Fecal Microbiota," Allergology Int. 2014;63:575-585.

International Search Report for PCT Patent App. No. PCT/JP2019/012602 (dated Jun. 18, 2019).

Baldassarre, M. E., et al., "Administration of a Multi-Strain Probiotic Product to Women in the Perinatal Period Differentially Affects the Breast Milk Cytokine Profile and May Have Beneficial Effects on Neonatal Gastrointestinal Functional Symptoms. A Randomized Clinical Trial," Nutrients 2016;8(677):1-13.

Mohan, T., et al., "CCL28 chemokine: an anchoring point bridging innate and adaptive immunity," Int. Immunopharmacol. 2017;51:165-170.

Matsuo, K., et al., "CCL28-Deficient Mice Have Reduced IgA Antibody-Secreting Cells and an Altered Microbiota in the Colon," J. Immunol. 2018;200:800-809.

Yang, G.-Y., et al., "Influence of orally fed a select mixture of Bacillus probiotics on intestinal T-cell migration in weaned MUC4 resistant pigs following *Escherichia coli* challenge," Vet. Res. 2016;47(71):1-15.

Meurens, F., et al., "Commensal Bacteria and Expression of Two Major Intestinal Chemokines, TECK/CCL25 and MEC/CCL28, and Their Receptors," PLoS ONE 2007;2(7):e677.

Pallister, K. B., et al., "Bovine CCL28 Mediates Chemotaxis via CCR10 and Demonstrates Direct Antimicrobial Activity against Mastitis Causing Bacteria," PLoS ONE 2015;10(9):e0138084.

Castelletti, E., et al., "The Mucosae-Associated Epithelial Chemokine (MEC/CCL28) Modulates Immunity in HIV Infection," PLoS ONE 2007;2(10):e969.

Seki, M., et al., "Galectin-9 suppresses the generation of Th17, promotes the induction of regulatory T cells, and regulates experimental autoimmune arthritis," Clin. Immunol. 2008;127:78-88.

De Kivit, S., et al., "Galectin-9 induced by dietary synbiotics is involved in suppression of allergic symptoms in mice and humans," Allergy 2012;67:343-352.

Fukushima, Y., et al., "Effect of bifidobacteria feeding on fecal flora and production of immunoglobulins in lactating mouse," Int. J. Food Microbiol. 1999;46:193-197.

* cited by examiner

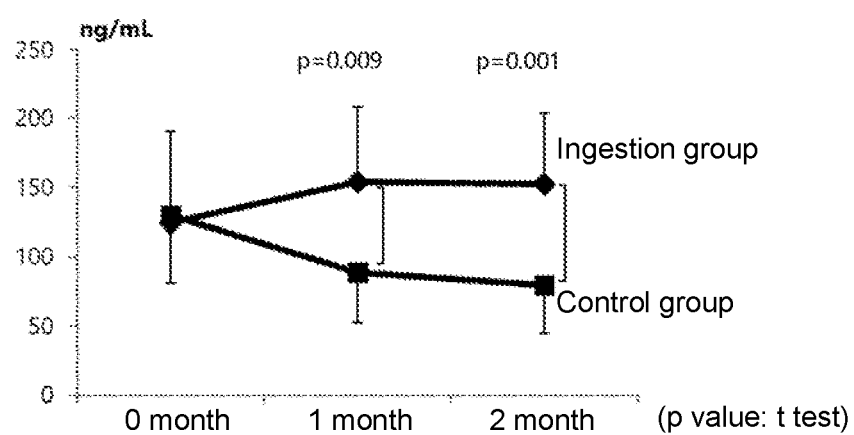

_US 11,730,171 B2_

COMPOSITION FOR ENHANCING BREAST MILK COMPONENT

This application is a national phase entry under 35 U.S.C. § 371 of PCT Patent Application No. PCT/JP2019/012602, filed on Mar. 25, 2019, which claims priority under 35 U.S.C. § 119 to Japanese Patent Application No. 2018-056597, filed Mar. 23, 2018, both of which are incorporated by reference.

These strains may be obtained from, for example, American Type Culture Collection (ATCC, Address: 10801 University Boulevard, Manassas, Va. 20110, United States of America), Belgian Coordinated Collections of Microorganisms (BCCM, Address: Rue de la Science 8, 1000 Brussels, Belgium), or a depository in which each strain is deposited.

TECHNICAL FIELD

The present invention relates to a composition that may be used for a specific use application, such as a composition for enhancing a breast milk component.

BACKGROUND ART

So-called Bifidobacteria such as *Bifidobacterium longum* or *Bifidobacterium breve* have been known as probiotics. For example, it has been reported that when Bifidobacteria are administered to a subject, the amount of immune-related micro RNAs (miRNAs) or mRNAs of immune-related genes increases/decreases in breast milk of the corresponding subject, thereby affecting the immunoregulatory action of the breast milk (Patent Literatures 1 to 2). It has been known that when probiotics including Bifidobacteria are administered to a subject, the amount of components suppressing the allergic onset of an offspring, such as IL-10 or TGF-$\beta$, increases in breast milk of the corresponding subject (Non-Patent Literature 1).

Indigestible oligosaccharides such as fructooligosaccharides have been known as prebiotics. For example, the indigestible oligosaccharides have been known to promote growth of beneficial bacteria such as Bifidobacteria. It has been reported that when the fructooligosaccharides are administered to a subject, the amount of interleukin 27 (IL-27) increases in the breast milk of the corresponding subject, and thus it is possible to prevent the allergic onset of a newborn baby who ingested the corresponding breast milk (Patent Literature 3).

CCL28 is a type of CC chemokine, and is constantly expressed in epidermal cells of mucosal tissues of a large intestine, a salivary gland, a mammary gland, and bronchial tubes. CCL28 promotes IgA production by causing migration of IgA-producing cells via CCR10 or has an antibacterial activity, and thus is considered to play an important role in innate immunity and acquired immunity in the mucosal tissues (Non-Patent Literature 2). Since the composition of the intestinal flora of CCL28 gene-deficient mice is different from that of the intestinal flora of wild-type mice, it is thought that CCL28 is also involved in the formation of the intestinal flora (Non-Patent Literature 3). Therefore, it is thought that CCL28 has an effect of preventing the infection of pathogenic bacteria or viruses or an effect of adjusting intestinal flora. Until now, it has been reported that in animal experiments, CCL28 expression is promoted in the small intestine by ingestion of bacteria of the genus *Bacillus* or *Escherichia coli* (Non-Patent Literatures 4 to 5). CCL28 is also secreted in breast milk, and thus is considered to contribute to prevention of mastitis (Non-Patent Literature 6). It has been reported that in infants infected with HIV, the higher the concentration of CCL28 in the ingested breast milk, the higher the survival rate (Non-Patent Literature 7). From this, it is thought that an increase of CCL28 contained in breast milk also leads to prevention of infection in infants.

It has been known that Galectin-9 is one of the proteins belonging to a lectin family having a high affinity with $\beta$-galactoside, and has an effect of suppressing the allergic onset (Non-Patent Literature 8). It has been known that the concentration of Galectin-9 in serum rises by ingestion of milk powder containing probiotics (Non-Patent Literature 9). It has not been known, however, that the concentration of Galectin-9 in breast milk increases by ingestion of probiotics.

CITATION LIST

Patent Literature

Patent Literature 1: WO2011/007815
Patent Literature 2: WO2012/096272
Patent Literature 3: JP-A-2013-245174

Non-Patent Literature

Non-Patent Literature 1: Baldassarre M E et al. Nutrients 8(11). (2016)
Non-Patent Literature 2: Mohan T et al. Int Immunopharmacol. 51:165-170. (2017)
Non-Patent Literature 3: Matsuo K et al. J Immunol. 200 (2):800-809. (2018)
Non-Patent Literature 4: Yang G Y et al. Vet Res. 47(1):71 (2016)
Non-Patent Literature 5: Meurens Fetal. PLoS One. 2(7): e677. (2007)
Non-Patent Literature 6: Pallister K B et al. PLoS One. 10(9):e0138084. (2015)
Non-Patent Literature 7: Castelletti E et al. PLoS One. 2(10):e969. (2007)
Non-Patent Literature 8: Seki M et al. Clin Immunol. 127(1):78-88. (2008)
Non-Patent Literature 9: de Kivit S et al. Allergy. 67(3): 343-52. (2012)

SUMMARY OF INVENTION

Technical Problem

An object of the present invention is to provide a composition that may be used for a specific use application, such as a composition for enhancing a breast milk component.

Means to Solve the Problem

The present inventors have found that when *Bifidobacterium longum* and *Bifidobacterium breve*, in combination with prebiotics such as fructooligosaccharides, are orally administered to a subject, the amount of a particular component in breast milk increases. Also, the present inventors have found that when a bacterium of the genus *Bifidobacterium* such as *Bifidobacterium breve* is orally administered to a subject, the amount of Galectin-9 in breast milk increases. Also, the present inventors have found that when a bacterium of the genus *Bifidobacterium* such as *Bifidobacterium breve* is orally administered to a subject, secretion of CCL28 is promoted. The present inventors have completed the present invention on the basis of these findings.

That is, the present invention may be exemplified as follows.

One aspect of the present invention is a composition for enhancing a breast milk component, which contains a bacterium of the genus *Bifidobacterium* as an active ingredient.

In a preferred aspect, in the composition, the breast milk component is at least one type of component selected from heat-shock protein, chemokine, interferon, and lectin.

In a preferred aspect, in the composition, the breast milk component is at least one type of component selected from HSP70, CCL8, CCL21, CCL28, IFN-γ, and galectin 9.

One aspect of the present invention is a composition for enhancing galectin 9 in breast milk, which contains a bacterium of the genus *Bifidobacterium* as an active ingredient.

One aspect of the present invention is a composition for promoting CCL28 secretion, which contains a bacterium of the genus *Bifidobacterium* as an active ingredient.

In a preferred aspect, the composition further contains a prebiotic.

In a preferred aspect, in the composition, the prebiotic is an oligosaccharide.

In a preferred aspect, in the composition, the prebiotic is a fructooligosaccharide.

In a preferred aspect, in the composition, the bacterium of the genus *Bifidobacterium* is *Bifidobacterium longum* and/or *Bifidobacterium breve*.

In a preferred aspect, in the composition, the bacterium of the genus *Bifidobacterium* is *Bifidobacterium longum* and *Bifidobacterium breve*.

In a preferred aspect, in the composition, the bacterium of the genus *Bifidobacterium* is *Bifidobacterium breve*.

In a preferred aspect, in the composition, the *Bifidobacterium longum* is *Bifidobacterium longum* BB536 (NITE BP-02621).

In a preferred aspect, in the composition, the *Bifidobacterium breve* is *Bifidobacterium breve* M-16V (NITE BP-02622).

In a preferred aspect, the composition is administered to a pregnant woman or a lactating woman.

In a preferred aspect, the composition is used by being administered to a first subject for the purpose of any one of followings (1) to (3) in a second subject to which breast milk of the first subject is administered:

(1) prevention and/or treatment of allergy;
(2) prevention and/or treatment of an infectious disease; and
(3) adjustment of intestinal flora.

In a preferred aspect, in the composition, the first subject is a pregnant woman or a lactating woman, and the second subject is an infant.

In a preferred aspect, the composition is a food/drink composition.

One aspect of the present invention is a method of enhancing a breast milk component, which includes a step of administering a bacterium of the genus *Bifidobacterium* to a subject.

In a preferred aspect, in the method, the breast milk component is at least one type of component selected from heat-shock protein, chemokine, interferon, and lectin.

In a preferred aspect, in the method, the breast milk component is at least one type of component selected from HSP70, CCL8, CCL21, CCL28, IFN-γ, and galectin 9.

One aspect of the present invention is a method of enhancing galectin 9 in breast milk, which includes a step of administering a bacterium of the genus *Bifidobacterium* to a subject.

One aspect of the present invention is a method of promoting CCL28 secretion, which includes a step of administering a bacterium of the genus *Bifidobacterium* to a subject.

In a preferred aspect, the method further includes a step of administering a prebiotic to the subject.

In a preferred aspect, in the method, the prebiotic is an oligosaccharide.

In a preferred aspect, in the method, the prebiotic is a fructooligosaccharide.

In a preferred aspect, in the method, the bacterium of the genus *Bifidobacterium* is *Bifidobacterium longum* and/or *Bifidobacterium breve*.

In a preferred aspect, in the method, the bacterium of the genus *Bifidobacterium* is *Bifidobacterium longum* and *Bifidobacterium breve*.

In a preferred aspect, in the method, the bacterium of the genus *Bifidobacterium* is *Bifidobacterium breve*.

In a preferred aspect, in the method, the *Bifidobacterium longum* is *Bifidobacterium longum* BB536 (NITE BP-02621).

In a preferred aspect, in the method, the *Bifidobacterium breve* is *Bifidobacterium breve* M-16V (NITE BP-02622).

In a preferred aspect, in the method, the subject is a pregnant woman or a lactating woman.

One aspect of the present invention is a method of producing milk powder for enhancing a breast milk component, which includes the following steps (A) to (C):

(A) a step of culturing a bacterium of the genus *Bifidobacterium* in a culture medium containing a milk component to obtain a culture;

(B) a step of subjecting the culture to spray-drying and/or freeze-drying to obtain microbial cell powder; and (C) a step of mixing the microbial cell powder with a prebiotic to obtain the milk powder for enhancing the breast milk component.

One aspect of the present invention is a method of producing milk powder for enhancing a breast milk component, which includes the following step (A):

(A) a step of mixing a prebiotic, a bacterium of the genus *Bifidobacterium*, and a milk component to obtain the milk powder.

In a preferred aspect, in the method, the milk component is a milk protein.

In a preferred aspect, in the method, the milk protein is at least one component selected from the group consisting of whey, whey hydrolysate, and casein.

One aspect of the present invention is a method of producing a supplement for enhancing a breast milk component, which includes the following steps (A) and (B):

(A) a step of mixing a prebiotic, a bacterium of the genus *Bifidobacterium*, and an excipient to obtain a mixture; and (B) a step of tableting the mixture.

In a preferred aspect, in the method, the bacterium of the genus *Bifidobacterium* is *Bifidobacterium longum* and/or *Bifidobacterium breve*.

In a preferred aspect, in the method, the prebiotic is a fructooligosaccharide.

In a preferred aspect, in the method, the milk powder or the supplement is used by being administered to a pregnant woman or a lactating woman.

BRIEF DESCRIPTION OF DRAWINGS

FIG. 1 shows the influence on CCL28 concentration in breast milk, by ingestion of a *Bifidobacterium breve* M-16V strain.

DESCRIPTION OF EMBODIMENTS

Hereinafter, the present invention will be described in detail.

<1> Active Ingredient

In the present invention, a bacterium of the genus *Bifidobacterium* is used as an active ingredient.

In the present invention, also, a prebiotic may be used as an active ingredient.

That is, the bacterium of the genus *Bifidobacterium* and the prebiotic, only when the prebiotic is used as the active ingredient as for the prebiotic, are also collectively referred to as "active ingredient."

The active ingredient may be, for example, a combination of *Bifidobacterium longum, Bifidobacterium breve*, and prebiotic.

In one aspect, by using the active ingredient, specifically, by administering the active ingredient to a subject, it is possible to increase the content of a particular component in the breast milk in the corresponding subject. That is, in one aspect, by using the active ingredient, specifically, by administering the active ingredient to the subject, it is possible to obtain an effect of increasing the content of a particular component in the breast milk in the corresponding subject. This effect is also referred to as a "breast milk component enhancing effect." An increase in the content of a particular component in the breast milk is also referred to as "enhancement of the breast milk component." The breast milk in which the content of the particular component is increased in this manner is also referred to as "breast milk of the present invention." The breast milk of the present invention is, specifically, breast milk of the subject administered with the active ingredient, that is, breast milk produced by the subject administered with the active ingredient. Specifically, the active ingredient may be administered to the subject in a manner described in a "method of the present invention" to be described below.

The particular component (the breast milk component to be enhanced) may include a protein. The protein may include heat-shock proteins, chemokines, interferons, and lectins. The heat-shock protein may include HSP70. The chemokine may include CC chemokines. The CC chemokine may include CCL8 (also called "MCP-2"), CCL21 (also called "6Ckine"), and CCL28 (also called "MEC"). The interferon may include interferon γ (IFN-γ). The lectin may include galectins. The galectin may include Galectin-9. That is, specifically, the particular component may include, HSP70, CCL8, CCL21, CCL28, IFN-γ, and Galectin-9. In one aspect, particularly, the particular component may include heat-shock proteins, chemokines, and interferons. In one aspect, more particularly, the particular component may include HSP70, CCL8, CCL21, and IFN-γ. For example, when the active ingredient is a combination of *Bifidobacterium longum, Bifidobacterium breve*, and prebiotic, particularly, the particular component may include heat-shock proteins, chemokines, and interferons. For example, when the active ingredient is a combination of *Bifidobacterium longum, Bifidobacterium breve*, and prebiotic, more particularly, the particular component may include HSP70, CCL8, CCL21, and IFN-γ. In one aspect, particularly, the particular component may include CCL28. In one aspect, particularly, the particular component may include Galectin-9. As the particular component, the content of one type of component may be increased, and the content of two or more types of components may be increased. In one aspect, a case where the particular component is interleukin, particularly, a case where the particular component is interleukin 27 (IL-27) or interleukin 10 (IL-10), may be excluded from the present invention. In one aspect, a case where the particular component is RNA may be excluded from the present invention. For example, when the active ingredient is not a combination of *Bifidobacterium longum, Bifidobacterium breve*, and prebiotic, a case where the particular component is RNA may be excluded from the present invention.

In one aspect, by using the active ingredient, specifically, by administering the active ingredient to the subject, secretion of CCL28 may be promoted. That is, in one aspect, by using the active ingredient, specifically, by administering the active ingredient to the subject, an effect of promoting secretion of CCL28 may be obtained. This effect is also called a "CCL28 secretion promoting effect." The secretion may include secretion in mucosal tissues, secretion in a mammary gland, and secretion into breast milk. By promoting CCL28 secretion in the mucosal tissues, for example, effects such as an antibacterial effect, an antiviral effect, and activation of an immune function may be obtained. The activation of the immune function may include promotion of IgA secretion. By the antibacterial effect, the antiviral effect, or the activation of the immune function, for example, an infectious disease may be prevented and/or treated. The infectious disease may include infectious gastroenteritis, upper respiratory infection, oral infection, uterine infection, and mastitis. By promoting CCL28 secretion in the mucosal tissues, for example, intestinal flora may be adjusted. By promoting CCL28 secretion in the mammary gland, for example, mastitis may be prevented and/or treated. In one aspect, a case where mastitis is prevented and/or treated by transfer of bacteria of the genus *Bifidobacterium* to the mammary gland may be excluded from the present invention. By promoting CCL28 secretion into breast milk, the content of CCL28 in the breast milk may be increased. Such an increase of the CCL28 content in the breast milk is also an example of the enhancement of the breast milk component. Breast milk in which the CCL28 content is increased in this manner is also an example of the breast milk of the present invention.

By using the breast milk of the present invention, specifically, by administering the breast milk of the present invention to the subject, various effects may be obtained in the corresponding subject. Such an effect is also called an "effect of the breast milk of the present invention." For convenience of explanation, a subject to which the active ingredient is administered is also called a "first subject," and a subject to which the breast milk of the present invention is administered is also called a "second subject." That is, the breast milk of the present invention is breast milk of the first subject administered with the active ingredient, and the effect of the breast milk of the present invention is an effect obtained in the second subject. The effect of the breast milk of the present invention may be an effect depending on the type or content of the breast milk component to be enhanced. For example, when heat-shock proteins such as HSP70 are enhanced, the expected effect may include promotion of digestive tract development, promotion of formation of tight junctions in a digestive tract, and maintenance of a barrier function of a digestive tract (Liedel J L. et al., Mother's milk-induced Hsp70 expression preserves intestinal epithelial barrier function in an immature rat pup model. Pediatr Res. 2011 May; 69 (5 Pt 1): 395-400). For example, when chemokines such as CCL8, CCL21, and CCL28 are enhanced, the expected effect may include an antibacterial effect, an antiviral effect, and activation of an immune function (Gong W. et al., Monocyte chemotactic protein-2 activates CCR5 and blocks CD4/CCR5-mediated HIV-1 entry/replication. J Biol Chem. 1998 Feb. 20; 273(8): 4289-92; Yang D. et al., Many chemokines including CCL20/MIP-3alpha display antimicrobial activity. J Leukoc Biol. 2003 September; 74(3): 448-55; Yuan Lin et al., CCL21 Cancer Immunotherapy. Cancers (Basel). 2014 June; 6(2): 1098-1110). The activation of the immune function may include promotion of IgA secretion. By the antibacterial effect, the antiviral effect, or the activation of the immune function, for example, an infectious disease may be prevented and/or treated. The infectious disease may include infectious gastroenteritis, upper respiratory infection, oral infection, uterine infection, and mastitis. When chemokines such as CCL8, CCL21, and CCL28 are enhanced, the expected effect may also include adjustment of intestinal flora. For example, when interferons such as IFN-γ are enhanced, the expected effect may include induction of a Th1-type immune response or suppression of allergy. For example, when lectins such as Galectin-9 are enhanced, the expected effect may include suppression of allergy. The suppression of allergy may include prevention or treatment of allergy. Specifically, the breast milk of the present invention may be administered to the subject in the manner described in "use of the breast milk of the present invention" to be described below.

The breast milk component enhancing effect may be confirmed by measuring the content of the particular component in breast milk at the time of administration of the active ingredient. Specifically, the breast milk component enhancing effect may be confirmed by measuring and comparing the content of the particular component in the breast milk at the time of non-administration of the active ingredient and at the time of administration of the active ingredient. That is, when the content of the particular component in the breast milk is increased at the time of administration of the active ingredient as compared to that at the time of non-administration of the active ingredient, it may be determined that the breast milk component enhancing effect is obtained. The content of the particular component may be confirmed by, for example, a conventionally known method used for quantifying a compound. Such a method may include, for example, GC/MS, NMR, ELISA, and a multi-item simultaneous detecting system (Multiplex).

The effect of the breast milk of the present invention may be confirmed by measuring the presence/absence or the extent of a phenomenon corresponding to the corresponding effect at the time of administration of the breast milk of the present invention. Specifically, the effect of the breast milk of the present invention may be confirmed by measuring and comparing the presence/absence or the extent of the phenomenon corresponding to the corresponding effect at the time of non-administration of the breast milk of the present invention, and at the time of administration of the breast milk of the present invention.

The CCL28 secretion promoting effect or the effect obtained therefrom may be confirmed in the same manner as the breast milk component enhancing effect or the effect of the breast milk of the present invention.

The present invention provides the use of the active ingredient in the application according to the breast milk component enhancing effect or the CCL28 secretion promoting effect. That is, the present invention provides, for example, the use of the active ingredient in enhancing the breast milk component, the use of the active ingredient in promoting CCL28 secretion, the use of the active ingredient in obtaining an effect obtained by promotion of CCL28 secretion, the use of the active ingredient in obtaining the effect of the breast milk of the present invention, the use of the active ingredient in producing the breast milk of the present invention, and the use of the active ingredient in producing the composition of the present invention such as a composition for enhancing a breast milk component or a composition for promoting CCL28 secretion. The present invention provides the active ingredient for use in the application according to the breast milk component enhancing effect or the CCL28 secretion promoting effect. That is, the present invention provides, for example, the active ingredient for use in enhancing the breast milk component, the active ingredient for use in promoting CCL28 secretion, the active ingredient for use in obtaining an effect obtained by promotion of CCL28 secretion, the active ingredient for use in obtaining the effect of the breast milk of the present invention, the active ingredient for use in producing the breast milk of the present invention, and the active ingredient for use in producing the composition of the present invention such as a composition for enhancing a breast milk component or a composition for promoting CCL28 secretion.

When a combination of ingredients is used as the active ingredient, the present invention provides the use of each active ingredient to be used in combination with other active ingredient(s). When a combination of ingredients is used as the active ingredient, the present invention provides each active ingredient to be used in combination with other active ingredient(s). Each active ingredient may be used in combination with other active ingredient (s) in the application according to the breast milk component enhancing effect or the CCL28 secretion promoting effect.

Both the active ingredient and the breast milk of the present invention may be used for therapeutic purposes, or used for non-therapeutic purposes. That is, unless otherwise specified, all the above exemplified effects may be obtained for therapeutic purposes, or may be obtained for non-therapeutic purposes. In the case of the non-therapeutic purposes, the phrase "treat" referred to in this specification is construed as "improve." The phrase "therapeutic purpose" may mean that, for example, an act of treating a human body for treatment is included, or particularly, may mean being performed as a medical practice. The phrase "non-therapeutic purpose" may mean that, for example, an act of treating a human body for treatment is not included, or particularly, may mean being performed as a non-medical practice. The non-therapeutic purpose may include purposes such as health promotion or beauty.

<Bacteria of Genus *Bifidobacterium*>

The bacterium of the genus *Bifidobacterium* is not particularly limited as long as a desired effect such as a breast milk component enhancing effect may be obtained. Specifically, the bacterium of the genus *Bifidobacterium* is not particularly limited as long as a desired effect such as a breast milk component enhancing effect may be obtained independently, or when used in combination with other active ingredients. The bacterium of the genus *Bifidobacterium* may include *Bifidobacterium longum*, *Bifidobacterium breve*, *Bifidobacterium bifidum*, *Bifidobacterium adolescentis*, *Bifidobacterium angulatum*, *Bifidobacterium dentium*, *Bifidobacterium pseudocatenulatum*, *Bifidobacterium animalis*, *Bifidobacterium pseudolongum*, and *Bifidobacterium thermophilum*. Particularly, the bacterium of the genus *Bifidobacterium* may include *Bifidobacterium longum* or *Bifidobacterium breve*, *Bifidobacterium animalis* subsp. *lactis*, and *Bifidobacterium bifidum*. More particularly, the bacterium of the genus *Bifidobacterium* may include *Bifidobacterium breve*. As for the bacterium of the genus *Bifidobacterium*, one type of bacterium may be used, or two or more types of bacteria may be used in combination. That is, as for the bacterium of the genus *Bifidobacterium*, for example, *Bifidobacterium longum* and/or *Bifidobacterium breve* may be used. In one aspect, as for the bacterium of the genus *Bifidobacterium*, particularly, *Bifidobacterium longum* and *Bifidobacterium breve* may be used in combination.

The *Bifidobacterium longum* also includes strains classified by any subspecies of the *Bifidobacterium longum*, such as *B. longum* subsp. *longum*, *B. longum* subsp. *infantis*, and *B. longum* subsp. *suis*. The *Bifidobacterium animalis* also includes strains classified by any subspecies of the *Bifidobacterium animalis*, such as *B. animalis* subsp. *lactis*. The *Bifidobacterium pseudolongum* also includes strains classified by any subspecies of the *Bifidobacterium pseudolongum*, such as *B. pseudolongum* subsp. *globosum*, or *B. pseudolongum* subsp. *pseudolongum*.

The *Bifidobacterium longum* is not particularly limited as long as a desired effect such as a breast milk component enhancing effect may be obtained. Specifically, the *Bifidobacterium longum* is not particularly limited as long as a desired effect such as a breast milk component enhancing effect may be obtained independently, or when used in combination with other active ingredients. Specifically, the *Bifidobacterium longum* may include BB536 (BAA-999, NITE BP-02621), ATCC 15697, ATCC 15707, ATCC 25962, ATCC 15702, ATCC 27533, M-63, BG7, DSM 24736, SBT 2928, NCC 490 (CNCM I-2170), and NCC 2705 (CNCM I-2618). Particularly, the *Bifidobacterium longum* may include BB536. As for the *Bifidobacterium longum*, one type of strain may be used, or two or more types of strains may be used.

The *Bifidobacterium breve* is not particularly limited as long as a desired effect such as a breast milk component enhancing effect may be obtained. Specifically, the *Bifidobacterium breve* is not particularly limited as long as a desired effect such as a breast milk component enhancing effect may be obtained independently, or in use of combination with other active ingredients. Specifically, the *Bifidobacterium breve* may include M-16V (NITE BP-02622), MCC1274 (B-3, FERM BP-11175), ATCC 15700, B632 (DSM 24706), Bb99 (DSM 13692), ATCC 15698, DSM 24732, UCC2003, YIT4010, YIT4064, BBG-001, BR-03, C50, and R0070. Particularly, the *Bifidobacterium breve* may include M-16V, DSM 24732, and BBG-01. More particularly, the *Bifidobacterium breve* may include M-16V. As for the *Bifidobacterium breve*, one type of strain may be used, or two or more types of strains may be used.

Specifically, the *Bifidobacterium bifidum* may include ATCC 29521, OLB6378, and BF-1. Specifically, the *Bifidobacterium adolescentis* may include ATCC 15703. Specifically, the *Bifidobacterium dentium* may include DSM 20436. Specifically, the *Bifidobacterium animalis* may include DSM 10140, Bb-12, DN-173 010, GCL2505, and CNCM I-3446. Specifically, the *Bifidobacterium pseudolongum* may include JCM 5820 or ATCC 25526. Specifically, the *Bifidobacterium thermophilum* may include ATCC 25525.

*Bifidobacterium longum* BB536 was internationally deposited under the Budapest Treaty with a deposit number of NITE BP-02621 at Patent Microorganisms Depository Center, National Institute of Technology and Evaluation (Room No. 122, 2-5-8 Kazusakamatari Kisarazu Chiba 292-0818, Japan) on Jan. 26, 2018.

*Bifidobacterium breve* M-16V was internationally deposited under the Budapest Treaty with a deposit number of NITE BP-02622 at Patent Microorganisms Depository Center, National Institute of Technology and Evaluation (Room No. 122, 2-5-8 Kazusakamatari Kisarazu Chiba 292-0818, Japan) on Jan. 26, 2018.

These strains may be obtained from, for example, American Type Culture Collection (ATCC, Address: 12301 Parklawn Drive, Rockville, Md. 20852 P.O. Box 1549, Manassas, Va. 20108, United States of America), Belgian Coordinated Collections of Microorganisms (BCCM, Address: Rue de la Science 8, 1000 Brussels, Belgium), or a depository in which each strain is deposited.

The strain specified by the above-exemplified strain name is not limited to a strain itself that has been deposited or registered in a predetermined institution with the corresponding strain name (hereinafter, for convenience of explanation, also referred to as a "deposited strain"), but also includes a strain substantially equivalent thereto (also referred to as a "derivative strain" or an "induced strain"). That is, for example, the phrase "*Bifidobacterium longum* BB536" is not limited to a strain itself that has been deposited in the above depository with a deposit number of BB536, but also includes a strain substantially equivalent thereto. For each strain, the phrase "the strain substantially equivalent to the above deposited strain" refers to a strain belonging to the same species as the above deposited strain, in which a desired effect such as a breast milk component enhancing effect may be obtained independently, or when used in combination with other active ingredients, the nucleotide sequence of the 16SrRNA gene thereof is identical to the nucleotide sequence of the 16SrRNA gene of the above deposited strain (preferably 99.86% or more, more preferably 99.93% or more, further preferably 100%), and further preferably, the mycological properties are the same as the above deposited strain. For each strain, the strain substantially equivalent to the above deposited strain may be, for example, a derivative strain whose parent strain is the corresponding deposited strain. The derivative strain may include a strain bred from the deposited strain or a strain naturally occurring from the deposited strain. A breeding method may include modifications by genetic engineering techniques, or modifications by inducing mutation(s). Methods of inducing mutation(s) may include X-ray irradiation, ultraviolet irradiation, and treatment with a mutagenic agent such as N-methyl-N'-nitro-N-nitrosoguanidine (MNNG), ethyl methane sulfonate (EMS), and methyl methane sulfonate (MMS). The strain naturally occurring from the deposited strain may include a strain naturally occurring when the deposited strain is used. Such a strain may include a mutant strain naturally occurring by culturing (for example, subculturing) of the deposited strain. The derivative strain may be constructed through one type of modification, or may be constructed through two or more types of modifications.

As the bacterium of the genus *Bifidobacterium*, a commercially available product may be used, or one acquired by appropriate production may be used. The commercially available product may include, for example, *Bifidobacterium longum* subspecies *longum* BB536 or *Bifidobacterium breve* M-16V, manufactured by Morinaga Milk Industry Co., Ltd. Microbial cells of the bacterium of the genus *Bifidobacterium* may be easily acquired by culturing the bacterium of the genus *Bifidobacterium*. The culturing method is not particularly limited as long as the bacterium of the genus *Bifidobacterium* can grow. As for the culturing method, for example, a method generally used for culturing the bacterium of the genus *Bifidobacterium* may be used as it is or after being properly modified. The culturing temperature may be, for example, 25° C. to 50° C., preferably 35° C. to 42° C. The culturing may be preferably carried out under anaerobic conditions, and may be carried out while, for example, an anaerobic gas such as a carbon dioxide gas is aerated. Also, the culturing may also be carried out under slightly aerobic conditions in liquid static culture. The culturing may be carried out, for example, until the bacterium of the genus *Bifidobacterium* grow to a desired degree.

A culture medium used for culturing is not particularly limited as long as the bacterium of the genus *Bifidobacterium* can grow. As for the culture medium, for example, a culture medium generally used for culturing the bacterium of the genus *Bifidobacterium* may be used as it is or after being properly modified. That is, as for carbon sources, for example, saccharides such as galactose, glucose, fructose, mannose, cellobiose, maltose, lactose, sucrose, trehalose, starch, starch hydrolysate, and molasses may be used depending on the assimilability. As for nitrogen sources, for example, ammonia, ammonium salts such as ammonium sulfate, ammonium chloride, and ammonium nitride, or nitrates may be used. Also, as for inorganic salts, for example, sodium chloride, potassium chloride, potassium phosphate, magnesium sulfate, calcium chloride, calcium nitride, manganese chloride, and ferrous sulfate may be used. Also, as for culture medium components, organic components such as peptone, soybean powder, defatted soybean meal, meat extract, and yeast extract may be used. Also, as for the culture medium components, milk components may be used. The milk component may include milk proteins. The milk protein may include casein, whey, and decomposition products thereof. These components may be used alone or in appropriate combination. Also, specifically, the culture medium generally used for culturing the bacterium of the genus *Bifidobacterium* may include a Reinforced Clostridial medium, an MRS medium (de Man, Rogosa, and Sharpe medium), an mMRS medium (modified MRS medium), a TOSP medium (TOS propionate medium), and a TOSP Mup medium (TOS propionate mupirocin medium).

As for the bacterium of the genus *Bifidobacterium*, microbial cells of the bacterium of the genus *Bifidobacterium* or a fraction containing the same may be used without particular limitation. That is, as for the bacterium of the genus *Bifidobacterium*, for example, the culture obtained by culturing may be used as it is, the culture may be used through dilution or concentration, or microbial cells collected from the culture may be used. Also, various additional operations such as heating or freeze-drying may be performed after culturing as long as a desired effect such as a breast milk component enhancing effect is not impaired. It is preferable that in the additional operations, the survival rate of the microbial cells is high. That is, specifically, the bacterium of the genus *Bifidobacterium* may include the culture of the bacterium of the genus *Bifidobacterium*, microbial cells collected from the same culture, and processed products such as a diluted product, a concentrate, and a dried product thereof. The microbial cells may be live cells or dead cells. The microbial cells may be composed of, for example, live cells, may be composed of dead cells, or may be a mixture of live cells and dead cells. In one aspect, the microbial cells may be used in a form containing live cells. In one aspect, the microbial cells may be composed of, for example, live cells, or may be a mixture of live cells and dead cells. For example, when the active ingredient is a combination of *Bifidobacterium longum*, *Bifidobacterium breve*, and prebiotic, the microbial cells may be used in a form containing live cells.

The treatment that may be used when live cells are used may include a bacterial fluid freezing method, a spray drying method, a freeze drying method, and an oil drop method. The dead cells may be prepared by subjecting live cells to, for example, a sterilization treatment. The sterilization treatment may include a heat treatment, a spray drying method, a retort sterilization method, a freeze drying method, an UHT sterilization method, a pressure sterilization method, a high pressure steam sterilization method, a dry heat sterilization method, a circulating steam sterilization method, an electromagnetic wave sterilization method, an electron beam sterilization method, a high frequency sterilization method, a radiation sterilization method, an ultraviolet sterilization method, an ethylene oxide gas sterilization method, a hydrogen peroxide gas plasma sterilization method, an alcohol sterilization method, a formalin fixation, and an electrolyzed water treatment method. The heat treatment may include heating at 70° C. to 100° C. for 10 to 60 min.

<Prebiotics>

The phrase "prebiotic" may mean an indigestible food ingredient that allows beneficial bacteria to selectively grow within an intestinal tract. The beneficial bacteria may include bacteria of the genus *Bifidobacterium*. That is, particularly, as for the prebiotic, an ingredient that selectively grows the bacterium of the genus *Bifidobacterium* is preferred. As for the prebiotic, one type of ingredient may be used, or two or more types of ingredients may be used in combination.

The prebiotic is not particularly limited as long as a desired effect such as a breast milk component enhancing effect may be obtained, specifically, as long as a desired effect such as a breast milk component enhancing effect may be obtained in use of combination with the bacterium of the genus *Bifidobacterium* (for example, *Bifidobacterium longum* and/or *Bifidobacterium breve*). The prebiotic may include oligosaccharides, dietary fiber, and gluconic acids. The oligosaccharide may include galactooligosaccharides, fructooligosaccharides, xylooligosaccharides, isomaltooligosaccharides, raffinose, lactulose, lactosucrose, soybean oligosaccharides, and coffee oligosaccharides. Also, the oligosaccharide may include human milk oligosaccharides. The human milk oligosaccharide may include: neutral human milk oligosaccharides such as 2'-fucosyllactose, 3-fucosyllactose, 2',3-difucosyllactose, lacto-N-triose II, lacto-N-tetraose, lacto-N-neotetraose, lacto-N-fucopentaose I, lacto-N-neofucopentaose, lacto-N-fucopentaose II, lacto-N-fucopentaose III, lacto-N-fucopentaose V, lacto-N-neofucopentaose V, lacto-N-difucohexaose I, lacto-N-difucohexaose II, 6'-galactosyllactose, 3'-galactosyllactose, lacto-N-hexaose, and lacto-N-neohexaose; or acidic human milk oligosaccharides such as 3'-sialyllactose, 6'-sialyllactose, 3-fucosyl-3'-sialyllactose, and disialyllacto-N-tetraose. The length of the oligosaccharide may be, for example, 3 to 10 residues, 3 to 7 residues, or 3 to 5 residues. The fructooligosaccharide may include one in which one or more fructose residues are linked to a fructose residue of sucrose by $\beta(2\rightarrow1)$ bonds. Specifically, the fructooligosaccharide may include 1-kestose (also referred to as "$GF_2$"), nystose (also referred to as "$GF_3$"), and $1^F$-$\beta$-fructofuranosylnystose (also referred to as "$GF_4$"). The fructooligosaccharide may include, for example, one type, two types, or all three types of components selected from $GF_2$, $GF_3$, and $GF_4$. The dietary fiber may include polydextrose or inulin. Particularly, the prebiotic may include oligosaccharides. More particularly, the prebiotic may include fructooligosaccharides.

As the prebiotic, a commercially available product may be used, or one acquired by appropriate production may be used. A method of producing the prebiotic is not particularly limited. The prebiotic may be produced by, for example, a chemical synthesis, an enzyme reaction, a fermentation method, an extraction method, or a combination thereof. The prebiotic may be purified to a desired degree. That is, as for the prebiotic, a purified product may be used, or a material containing the prebiotic may be used. As for the prebiotic, for example, those having a purity of 50% (w/w) or more, 70% (w/w) or more, 90% (w/w) or more, or 95% (w/w) or more may be used.

<2> Composition of the Present Invention

The composition of the present invention is a composition containing the above active ingredient.

That is, the composition of the present invention is a composition containing the bacterium of the genus *Bifidobacterium*.

The composition of the present invention may further contain a prebiotic.

The composition of the present invention may be a composition containing, for example, *Bifidobacterium longum*, *Bifidobacterium breve*, and prebiotic.

The composition of the present invention may be used by being administered to a subject. Specifically, the composition of the present invention may be administered to the subject in a manner described in the "method of the present invention" to be described below. The subject to which the composition of the present invention is administered is an example of a first subject (a subject to which the active ingredient is administered). The composition of the present invention may be used so as to obtain, for example, the above-exemplified effects.

In one aspect, by using the composition of the present invention, specifically, by administering the composition of the present invention to the subject, it is possible to increase the content of the particular component in the breast milk in the corresponding subject, that is, it is possible to obtain the breast milk component enhancing effect. That is, the composition of the present invention may be a composition for enhancing a breast milk component. In one aspect, the composition of the present invention may be a composition for enhancing a breast milk component wherein the composition contains *Bifidobacterium longum*, *Bifidobacterium breve*, and prebiotic. Also, in one aspect, the composition of the present invention may be a composition for enhancing Galectin-9 in breast milk wherein the composition contains the bacterium of the genus *Bifidobacterium*.

Also, in one aspect, by using the composition of the present invention, specifically, by administering the composition of the present invention to the subject, secretion of CCL28 may be promoted in the corresponding subject, that is, a CCL28 secretion promoting effect may be obtained. That is, the composition of the present invention may be a composition for promoting CCL28 secretion. That is, in one aspect, the composition of the present invention may be a composition for promoting CCL28 secretion wherein the composition contains the bacterium of the genus *Bifidobacterium*. Also, the composition of the present invention (specifically, the composition for promoting CCL28 secretion) may be a composition used for obtaining an effect obtained by promotion of CCL28 secretion. That is, the composition of the present invention (specifically, the composition for promoting CCL28 secretion) may be, for example, a composition for activating an antibacterial, antivirus, or immune function. Also, the composition of the present invention (specifically, the composition for promoting CCL28 secretion) may be, for example, a composition for promotion of IgA secretion. Also, the composition of the present invention (specifically, composition for promoting the CCL28 secretion) may be, for example, a composition for preventing and/or treating an infectious disease. Also, the composition of the present invention (specifically, the composition for promoting CCL28 secretion) may be, for example, a composition for preventing and/or treating mastitis. Also, in one aspect, a case where mastitis is prevented and/or treated by transfer of a bacterium of the genus *Bifidobacterium* to a mammary gland may be excluded from the composition of the present invention (specifically, the composition for promoting CCL28 secretion). The composition of the present invention (specifically, the composition for promoting CCL28 secretion) may be, for example, a composition for enhancing CCL28 in breast milk.

Also, by using the breast milk of the present invention, specifically, by administering the breast milk of the present invention to the subject, the effect of the breast milk of the present invention may be obtained in the corresponding subject. That is, the composition of the present invention may be a composition used for obtaining the effect of the breast milk of the present invention through the use of the breast milk of the present invention. That is, the composition of the present invention may be a composition that is used by being administered to the first subject for the purpose of obtaining the effect of the breast milk of the present invention in a second subject to which the breast milk of the first subject (the breast milk of the present invention) is administered. That is, the composition of the present invention may be, for example, a composition that is used by being administered to the first subject for the purpose of promoting digestive tract development, promoting formation of tight junctions in a digestive tract, or maintaining a barrier function of a digestive tract in the second subject. Also, the composition of the present invention may be, for example, a composition that is used by being administered to the first subject for the purpose of an antibacterial effect, an antiviral effect, or activation of an immune function in the second subject. Also, the composition of the present invention may be, for example, a composition that is used by being administered to the first subject for the purpose of promoting IgA secretion in the second subject. Also, the composition of the present invention may be, for example, a composition that is used by being administered to the first subject for the purpose of preventing and/or treating an infectious disease in the second subject. Also, the composition of the present invention may be, for example, a composition that is used by being administered to the first subject for the purpose of adjusting intestinal flora in the second subject. Also, the composition of the present invention may be, for example, a composition that is used by being administered to the first subject for the purpose of inducing a Th1-type immune response in the second subject. Also, the composition of the present invention may be, for example, a composition that is used by being administered to the first subject for the purpose of suppressing allergy in the second subject.

Regarding the subject to which the composition of the present invention is administered, the description on the subject to which the active ingredient is administered in the "method of the present invention" may be applied correspondingly. That is, the subject to which the composition of the present invention is administered may include female mammals such as humans (that is, female). Also, the subject to which the composition of the present invention is administered may include pregnant women or lactating women in the case of the human.

Regarding the subject to which the breast milk of the present invention is administered, the description on the subject to which the breast milk of the present invention is administered in "the use of the breast milk of the present invention" may be applied correspondingly. That is, the subject to which the breast milk of the present invention is administered may include mammals such as humans. Also, the subject to which the breast milk of the present invention is administered may include babies or infants in the case of the human.

Also, when a combination of ingredients is used as the active ingredient, as described above, each active ingredient may be used for use in combination with other active ingredients. That is, in another aspect, the composition of the present invention may be a composition containing at least one component (also referred to as a "selective component") selected from the active ingredients, and a composition to be used in combination with a remaining component selected from the active ingredients (also referred to as a "residual component"). In another aspect, the composition of the present invention may be a composition containing at least one component selected from, for example, *Bifidobacterium longum*, *Bifidobacterium breve*, and prebiotic, and a composition to be used in combination with a remaining component selected from *Bifidobacterium longum*, *Bifidobacterium breve*, and prebiotic. In another aspect, regarding the composition of the present invention, the above described description on the composition of the present invention may be applied correspondingly except for containing a selective component and using in combination with a residual component. In another aspect, the composition of the present invention may be used to obtain, for example, the above-exemplified effects. The residual component may be administered to the subject before administration of the composition, may be administered to the subject concurrently with the composition, or may be administered to the subject after administration of the composition. Regarding the timing for use in combination, the description on administration of the active ingredient in the "method of the present invention" may be applied correspondingly.

The composition of the present invention may be, for example, a food/drink composition, a pharmaceutical composition, or a feed composition. That is, the present invention may provide, for example, a food/drink composition for use in the above-exemplified application for breast milk component enhancement, CCL28 secretion promotion or the like, a pharmaceutical composition for use in the above-exemplified application for breast milk component enhancement, CCL28 secretion promotion, or the like, or a feed composition for use in the above-exemplified application for breast milk component enhancement, CCL28 secretion promotion, or the like. These compositions are also referred to as "a food/drink composition of the present invention," "a pharmaceutical composition of the present invention," and "a feed composition of the present invention," respectively. The composition of the present invention may consist of only the active ingredient, or may contain ingredients other than the active ingredient.

The ingredients other than the active ingredient are not particularly limited as long as a desired effect such as a breast milk component enhancing effect is not impaired. As for the ingredients other than the active ingredient, those which are acceptable depending on the usage form of the composition of the present invention may be used. As for the ingredients other than the active ingredient, for example, ingredients to be blended with foods and drinks, pharmaceuticals, or feeds in use may be used. Specifically, the ingredients other than the active ingredient may include ingredients exemplified for the food/drink composition, the pharmaceutical composition, or the feed composition to be described below. As for the ingredients other than the active ingredient, one type of ingredient may be used, or two or more types of ingredients may be used in combination.

The content or the content ratio of each ingredient (that is, the active ingredient and optionally other ingredients) in the composition of the present invention is not particularly limited as long as a desired effect such as a breast milk component enhancing effect may be obtained. The content or the content ratio of each ingredient in the composition of the present invention may be properly set according to various conditions such as the type of the active ingredient, the types of other ingredients, the type, form (dosage form), and usage of the composition, and the type, age, and health condition of an administration target.

The amount of the bacterium of the genus *Bifidobacterium* in the composition of the present invention may be, for example, $1 \times 10^4$ cfu/g or more, $1 \times 10^5$ cfu/g or more, $1 \times 10^6$ cfu/g or more, or $1 \times 10^7$ cfu/g or more, may be $10^{13}$ cfu/g or less, $10^{12}$ cfu/g or less, or $1 \times 10^{11}$ cfu/g or less, or may fall within the range of combinations thereof. Also, the amount of the bacterium of the genus *Bifidobacterium* in the composition of the present invention may be, for example, $1 \times 10^4$ cfu/mL or more, $1 \times 10^5$ cfu/mL or more, $1 \times 10^6$ cfu/mL or more, or $1 \times 10^7$ cfu/mL or more, may be $10^{13}$ cfu/mL or less, $10^{12}$ cfu/mL or less, or $1 \times 10^{11}$ cfu/mL or less, or may fall within the range of combinations thereof. Specifically, the amount of the bacterium of the genus *Bifidobacterium* in the composition of the present invention may be, for example, $1 \times 10^4$ to $1 \times 10^{13}$ cfu/g or $1 \times 10^4$ to $1 \times 10^{13}$ cfu/ml, may be $1 \times 10^6$ to $1 \times 10^{12}$ cfu/g or $1 \times 10^6$ to $1 \times 10^{12}$ cfu/ml, or may be $1 \times 10^7$ to $1 \times 10^{11}$ cfu/g or $1 \times 10^7$ to $1 \times 10^{11}$ cfu/ml. Also, for example, when the composition of the present invention is a food/drink composition, the amount of the bacterium of the genus *Bifidobacterium* in the composition is preferably $1 \times 10^4$ to $1 \times 10^{13}$ cfu/g or $1 \times 10^4$ to $1 \times 10^{13}$ cfu/ml, and more preferably $1 \times 10^7$ to $1 \times 10^{11}$ cfu/g or $1 \times 10^7$ to $1 \times 10^{11}$ cfu/ml. Also, for example, when the composition of the present invention is a pharmaceutical composition, the amount of the bacterium of the genus *Bifidobacterium* in the composition of the present invention is preferably $1 \times 10^4$ to $1 \times 10^{13}$ cfu/g or $1 \times 10^4$ to $1 \times 10^{13}$ cfu/ml, and more preferably $1 \times 10^7$ to $1 \times 10^{11}$ cfu/g or $1 \times 10^7$ to $1 \times 10^{11}$ cfu/ml. Also, for example, when the composition of the present invention is a feed composition, the amount of the bacterium of the genus *Bifidobacterium* in the composition of the present invention is preferably $1 \times 10^6$ to $1 \times 10^{12}$ cfu/g or $1 \times 10^6$ to $1 \times 10^{12}$ cfu/ml, and more preferably $1 \times 10^7$ to $1 \times 10^{11}$ cfu/g or $1 \times 10^7$ to $1 \times 10^{11}$ cfu/ml. When two or more types of bacteria of the genus *Bifidobacterium* are used, the above-exemplified amount of the bacterium of the genus *Bifidobacterium* in the composition of the present invention may be a total amount of these two or more types of bacteria of the genus *Bifidobacterium*, or may be each amount. That is, specifically, when the bacterium of the genus *Bifidobacterium*, *Bifidobacterium longum* and *Bifidobacterium breve* are used in combination, for example, each of the *Bifidobacterium longum* and the *Bifidobacterium breve* in the composition of the present invention may be present within a range of the above exemplified amounts of the bacterium of the genus *Bifidobacterium* in the composition of the present invention. The phrase "cfu" indicates a colony forming unit. When the active ingredient is dead cells, the phrase "cfu" may be replaced with "cells."

The amount of the prebiotic in the composition of the present invention may be, for example, 1% (w/w) or more, 5% (w/w) or more, or 10% (w/w) or more, may be 90% (w/w) or less, 70% (w/w) or less, 50% (w/w) or less, 30%

(w/w) or less, 20% (w/w) or less, 10% (w/w) or less, or 5% (w/w) or less, or may fall within the range of consistent combinations thereof. Specifically, the amount of the prebiotic in the composition of the present invention may be, for example, 1% (w/w) to 90% (w/w), may be 1% (w/w) to 70% (w/w), may be 1% (w/w) to 50% (w/w), or may be 1% (w/w) to 20% (w/w). Also, for example, when the composition of the present invention is a food/drink composition, the amount of the prebiotic in the composition of the present invention is preferably 1 to 70% (w/w). Also, for example, when the composition of the present invention is a pharmaceutical composition, the amount of the prebiotic in the composition of the present invention is preferably 1 to 70% (w/w). Also, for example, when the composition of the present invention is a feed composition, the amount of the prebiotic in the composition of the present invention is preferably 1 to 70% (w/w). When two or more types of prebiotics are used, the above-exemplified amount of the prebiotic in the composition of the present invention may be a total amount of these two or more types of prebiotics. Also, when a material containing a prebiotic is used, unless otherwise specified, it is assumed that the content of the prebiotic is calculated on the basis of the amount of the prebiotic itself in the corresponding material.

Also, the amount of each active ingredient in the composition of the present invention may be set such that, for example, a dose of each active ingredient to be described below may be obtained.

The form of the composition of the present invention is not particularly limited. As for the form of the composition of the present invention, one which is acceptable depending on the usage form of the composition of the present invention may be employed. Specifically, the form of the composition of the present invention may include forms exemplified for the food/drink composition, the pharmaceutical composition, or the feed composition as described below.

The active ingredient and other ingredients may be present in the composition of the present invention by being mixed with each other or may be present in the composition of the present invention while being separate from each other or separate in any combinations. For example, when the composition of the present invention contains a plurality of active ingredients (for example, *Bifidobacterium longum*, *Bifidobacterium breve*, and prebiotic), the composition of the present invention may be provided as a set of the corresponding active ingredients in which each is packaged separately. In such a case, the corresponding active ingredients may be properly combined and administered to the subject.

<Food/Drink Composition>

The food/drink composition of the present invention is not particularly limited as long as the active ingredient is present. The food/drink composition of the present invention may be provided in any form such as liquids, pastes, gel-like solids, or powder.

The food/drink composition may be, for example, food or drink itself, or may be a material used for producing the food or the drink. Such a material may include seasonings, food additives, and other food/drink raw materials. Specifically, the food/drink composition may include flour products such as bread, macaroni, spaghetti, noodles, cake mix, frying powder, and bread crumbs; instant foods such as instant noodles, cup noodles, retort•cooked foods, cooked cans, microwave foods, instant soup•stew, instant miso soup•clear soup, canned soup, freeze-dried foods, and other instant foods; processed agricultural products such as canned agricultural products, canned fruits, jams•marmalades, pickles, boiled beans, dried agricultural products, and cereals (processed grain products); processed seafood products such as canned seafoods, fish hams•sausages, seafood paste foods, seafood delicacies, and tsukudani; processed livestock products such as canned livestock•pastes, and meat hams•sausages; milk•dairy products such as processed milk, dairy drinks, yogurts, lactic acid drinks, cheese, ice creams, powdered milk formulas, cream, and other dairy products; oils and fats such as butter, margarines, and vegetable oils; basic seasonings such as soy sauces, miso, sauces, processed tomato seasonings, mirins, and vinegars; complex seasonings•foods such as cooking mix, curry sauces, spicy soy sauces, dressings, mentsuyu, spices, and other complex seasonings; frozen foods such as frozen food ingredients, semi-cooked frozen foods, and cooked frozen foods; confectioneries such as caramels, candies, gummies, chewing gums, chocolates, cookies, biscuits, cakes, pies, snacks, crackers, Japanese sweets, rice confectionaries, bean confectionaries, dessert confectioneries, jellies, tablet confectioneries, and other confectioneries; favorite drinks such as carbonated drinks, natural fruit juices, fruit juice drinks, fruit juice-containing soft drinks, pulp drinks, granule-containing fruit drinks, vegetable-based drinks, soy milk, soy milk drinks, coffee drinks, tea drinks, powdered drinks, concentrated drinks, sports drinks, nutritional drinks, alcohol drinks, and other favorite drinks; other commercial foods such as liquid foods, weaning foods, sprinkles, and ochazuke seaweed; powdered milk formula for childcare; enteral nutritional foods; special purpose foods, health functional foods (foods for specified health uses, nutritional functional foods, and functionality labeled foods); and dietary supplements. Also, the food/drink composition may be a supplement, or may be, for example, a tablet-shaped supplement. When the food/drink composition is a supplement, the active ingredient may be taken without being affected by other foods in regard to the amount of food and the calorie intake per day.

The food/drink composition of the present invention may be produced by combining the active ingredient with other ingredients. An operation of combining the active ingredient with other ingredients is also called "addition of the active ingredient." A method of producing the food/drink composition of the present invention is not particularly limited. The food/drink composition of the present invention may be produced by, for example, the same method as normal food or drink by using the same raw materials as the normal food or drink except that the active ingredient is added. The same also applies to the case where the food/drink composition of the present invention is produced as a material used for producing food or drink, such as seasonings, food additives, or other food/drink raw materials. The addition of the active ingredient may be carried out at any stage in the food/drink composition producing process. The addition of the active ingredient may be carried out, for example, during production of the food/drink composition or after the production. That is, for example, the food/drink composition of the present invention may be obtained by adding the active ingredient to food or drink that is previously prepared. Also, the food/drink composition may be produced through a fermentation process with the added active ingredient (particularly, bacterium of the genus *Bifidobacterium*). The food/drink composition produced through the fermentation process may include fermented products such as lactic acid drinks or fermented milk. That is, the active ingredient (particularly, the bacterium of the genus *Bifidobacterium*) may be used as, for example, a starter for producing a fermented product. Also, the active ingredient may also be added later to the produced fermented product.

Also, another food/drink composition may also be produced by using the food/drink composition of the present invention. That is, for example, when the food/drink composition of the present invention is provided as a material used for producing food or drink, such as seasonings, food additives, or other food/drink raw materials, another food/drink composition may be produced by adding the food/drink composition of the present invention to raw materials of the food or the drink. The other food/drink composition produced in this manner is also an aspect of the food/drink composition of the present invention. Regarding addition of the food/drink composition of the present invention, the description on the addition of the active ingredient in the production of the food/drink composition may be applied correspondingly.

The food/drink composition of the present invention may be sold as a food/drink composition (for example, food or drink, or its material) labeled with the above-exemplified application such as enhancement of the breast milk component. That is, the food/drink composition of the present invention may be labelled with words such as "for enhancing the breast milk component." Words on the label are not limited to words indicating the above-exemplified application such as enhancement of the breast milk component, and may be words indicating effects occurring by the use of the composition in the above-exemplified application. For example, the effects occurring by the use of the composition in the application for enhancing the breast milk component may include effects of the breast milk of the present invention.

The above "label" means all actions of informing consumers of the above application. All labels correspond to the "label" of the present invention regardless of the purpose of a label, the contents of a label, and a target object and a medium of labeling as long as the above application may be recalled or analogized. However, it is preferable that labeling is made by an expression that allows the consumers to directly recognize the above application.

Specifically, as for labeling, an action of describing the above application on a product or a product packaging related to the food/drink composition of the present invention, an action of assignment and delivery of the product or the product packaging (on which the above application is described), and display and importation for the assignment or delivery, and an action of displaying or distributing advertisements, a price list, or a transaction document related to the product, on which the above application is described, or providing information having these as contents, on which the above application is described, by an electromagnetic (Internet, etc.) method may be exemplified. Particularly, labeling on packaging, containers, catalogs, pamphlets, advertising materials at a sales site such as POP, and other documents is preferred.

Also, as for the label, a label permitted by the government or the like (for example, a label that is approved in accordance with various systems specified by the government, and is applied in the form based on such approval) is preferred. As for such a label, labels for health functional foods, health foods, functional foods, enteral nutritional foods, special-purpose foods, dietary supplements, and quasi-drugs may be exemplified, and other labels approved by the Consumer Affairs Agency may also be exemplified. As for the label approved by the Consumer Affairs Agency, foods for specified health uses, nutritional functional foods, functionality labeled foods, and labels approved by systems similar to these may be exemplified. Specifically, as for the label approved by the Consumer Affairs Agency, labels for foods for specified health uses, labels for foods for conditional specified health uses, labels to the effect that the structure or function of a body is affected, labels on disease risk reduction, and labels for functionality based on scientific grounds may be exemplified. More specifically, as for the label approved by the Consumer Affairs Agency, labels for foods for specified health uses (particularly, labels for health applications), which are stipulated in Cabinet Office Ordinance (Cabinet Office Ordinance No. 57, Aug. 31, 2009) concerning permission, etc. for special application labeling prescribed in the Health Promotion Act, and labels similar thereto may be exemplified.

Specifically, the food composition of the present invention may be, for example, milk powder for enhancing the breast milk component. The milk powder for enhancing the breast milk component may be produced by, for example, the following method.

That is, the present invention provides a method of producing the milk powder for enhancing the breast milk component, which includes the following steps (A) to (C):

(A) a step of culturing a bacterium of the genus *Bifidobacterium* in a culture medium containing a milk component to obtain a culture;

(B) a step of subjecting the culture to spray-drying and/or freeze-drying to obtain microbial cell powder; and (C) a step of mixing the microbial cell powder with a prebiotic to obtain milk powder for enhancing the breast milk component.

Also, the present invention provides a method of producing the milk powder for enhancing the breast milk component, which includes the following step (A):

(A) a step of mixing a prebiotic, a bacterium of the genus *Bifidobacterium*, and a milk component to obtain milk powder.

Also, specifically, the food composition of the present invention may be, for example, a supplement for enhancing the breast milk component. The supplement for enhancing the breast milk component may be produced by, for example, the following method.

That is, the present invention provides a method of producing the supplement for enhancing the breast milk component, which includes the following steps (A) and (B):

(A) a step of mixing a prebiotic, a bacterium of the genus *Bifidobacterium*, and an excipient to obtain a mixture; and (B) a step of tableting the mixture.

In any of the above production methods, ingredients other than the ingredients mentioned in the above steps may be properly used in combination.

<Pharmaceutical Composition>

The pharmaceutical composition of the present invention is not particularly limited as long as the active ingredient is present. As for the pharmaceutical composition of the present invention, for example, the active ingredient may be used as it is, or the active ingredient may be properly formulated in use.

A dosage form of the pharmaceutical composition of the present invention is not particularly limited. Specifically, the dosage form may include tablets, pills, powder, solutions, suspensions, emulsions, granules, capsules, syrups, and suppositories. Also, in formulation, physiologically acceptable additives such as excipients, binders, disintegrants, lubricants, stabilizers, flavoring agents, diluents, surfactants, and solvents may be used. These additives may be properly selected according to various conditions such as a dosage form. The additive may include various organic components and inorganic components.

Examples of the excipient may include sugar derivatives such as lactose, sucrose, glucose, mannitol, and sorbitol; starch derivatives such as cornstarch, potato starch, α-starch, dextrin, and carboxymethyl starch; cellulose derivatives such as crystalline cellulose, hydroxypropylcellulose, hydroxypropylmethylcellulose, carboxymethylcellulose, and carboxymethylcellulose calcium; gum arabic; dextran; pullulan; silicate derivatives such as light anhydrous silicic acid, synthetic aluminum silicate, and magnesium aluminometasilicate; phosphate derivatives such as calcium phosphate; carbonate derivatives such as calcium carbonate; and sulfate derivatives such as calcium sulfate.

Examples of the binder may include gelatin; polyvinylpyrolidone; and macrogol in addition to the above excipients.

Examples of the disintegrator may include cellulose derivatives or chemically modified starch such as sodium croscarmellose, sodium carboxymethylstarch, and crosslinked polyvinylpyrrolidone in addition to the above excipients.

Examples of the lubricant may include talc; stearic acid; metallic stearates such as calcium stearate and magnesium stearate; colloidal silica; waxes such as bee gum and spermaceti; boric acid; glycol; carboxylic acids such as fumaric acid and adipic acid; carboxylic acid sodium salts such as sodium benzoate; sulfates such as sodium sulfate; leucine; lauryl sulfates such as sodium lauryl sulfate and magnesium lauryl sulfate; silicic acids such as silicic acid anhydride, and silicic acid hydrate; and starch derivatives.

Examples of the stabilizer may include paraoxybenzoic acid esters such as methylparaben, and propylparaben; alcohols such as chlorobutanol, benzylalcohol, and phenylethylalcohol; benzalkonium chloride; acetic anhydride; and sorbic acid.

Examples of the flavoring agent may include sweeteners, acidulants, and flavors.

<Feed Composition>

The feed composition of the present invention is not particularly limited as long as the active ingredient is present. The feed composition may include pet foods or livestock feeds. The feed of the present invention may be provided in any form such as powder, granules, crumbles, pellets, cubes, pastes, or liquids.

The feed composition of the present invention may be produced by combining the active ingredient with other ingredients. An operation of combining the active ingredient with other ingredients is also called "addition of the active ingredient." A method of producing the feed composition of the present invention is not particularly limited. The feed composition of the present invention may be produced by, for example, the same method as normal feed by using the same raw materials as the normal feed except that the active ingredient is added. The addition of the active ingredient may be carried out at any stage in the feed composition producing process. The addition of the active ingredient may be carried out, for example, during production of the feed composition or after the production. That is, for example, the feed composition of the present invention may be obtained by adding the active ingredient to feed that is previously prepared. Also, the feed composition may be produced through a fermentation process with the added active ingredient (particularly, the bacterium of the genus *Bifidobacterium*). The feed composition produced through the fermentation process may include silage.

<3> Method of The Present Invention

The method of the present invention is a method including a step of administering the above active ingredient to a subject. This step is also called an "administration step."

That is, the method of the present invention is a method including a step of administering a bacterium of the genus *Bifidobacterium* to a subject.

The method of the present invention may also include a step of administering a prebiotic to a subject.

The method of the present invention may be a method including a step of administering, for example, *Bifidobacterium longum, Bifidobacterium breve*, and prebiotic to a subject.

In one aspect, by the method of the present invention, specifically, by administering the active ingredient to a subject, it is possible to increase the content of a particular component in the breast milk in the corresponding subject, that is, it is possible to obtain a breast milk component enhancing effect. That is, the method of the present invention may be a method of enhancing a breast milk component (a particular component in the breast milk). In one aspect, the method of the present invention may be a method for enhancing the breast milk component, which includes a step of administering *Bifidobacterium longum, Bifidobacterium breve*, and prebiotic to the subject. Also, in one aspect, the method of the present invention may be a method for enhancing Galectin-9 in the breast milk, which includes a step of administering the bacterium of the genus *Bifidobacterium* to the subject.

Also, in one aspect, by the method of the present invention, specifically, by administering the active ingredient to the subject, secretion of CCL28 may be promoted in the corresponding subject, that is, a CCL28 secretion promoting effect may be obtained. That is, the method of the present invention may be a method of promoting secretion of CCL28. That is, in one aspect, the method of the present invention may be a method of promoting CCL28 secretion, which includes a step of administering the bacterium of the genus *Bifidobacterium* to the subject. Also, the method of the present invention (specifically, the method of promoting the CCL28 secretion) may be a method carried out to obtain an effect obtained by promotion of the CCL28 secretion. That is, the method of the present invention (specifically, the method of promoting the CCL28 secretion) may be, for example, a method of obtaining an antibacterial effect, a method of obtaining an antiviral effect, or a method of activating an immune function. Also, the method of the present invention (specifically, the method of promoting the CCL28 secretion) may be, for example, a method of promoting IgA secretion. Also, the method of the present invention (specifically, the method of promoting the CCL28 secretion) may be, for example, a method of preventing and/or treating an infectious disease. Also, the method of the present invention (specifically, the method of promoting the CCL28 secretion) may be, for example, a method of preventing and/or treating mastitis. In one aspect, a case where mastitis is prevented and/or treated by transfer of a bacterium of the genus *Bifidobacterium* to a mammary gland may be excluded from the method of preventing and/or treating mastitis. Also, the method of the present invention (specifically, the method of promoting the CCL28 secretion) may be, for example, a method of enhancing CCL28 in the breast milk.

Also, by using the breast milk of the present invention, specifically, by administering the breast milk of the present invention to the subject, the effect of the breast milk of the present invention may be obtained in the corresponding subject. That is, the method of the present invention may be a method carried out to obtain the effect of the breast milk of the present invention through the use of the breast milk of the present invention. That is, the method of the present invention may be a method carried out for the first subject for the purpose of obtaining the effect of the breast milk of the present invention in the second subject to which the breast milk of the first subject (the breast milk of the present invention) is administered. That is, the method of the present invention may be, for example, a method carried out for the first subject for the purpose of promoting digestive tract development, promoting formation of tight junctions in a digestive tract, or maintaining a barrier function of a digestive tract, in the second subject. Also, the method of the present invention may be, for example, a method carried out for the first subject for the purpose of an antibacterial effect, an antiviral effect, or activation of an immune function in the second subject. Also, the method of the present invention may be, for example, a method carried out for the first subject for the purpose of promoting IgA secretion in the second subject. Also, the method of the present invention may be, for example, a method carried out for the first subject for the purpose of preventing and/or treating an infectious disease in the second subject. Also, the method of the present invention may be, for example, a method carried out for the first subject for the purpose of adjusting intestinal flora in the second subject. Also, the method of the present invention may be, for example, a method carried out for the first subject for the purpose of inducing a Th1-type immune response in the second subject. Also, the method of the present invention may be, for example, a method carried out for the first subject for the purpose of suppressing allergy in the second subject.

The phrase "administering the active ingredient to the subject" may be synonymous with "making the subject ingest the active ingredient." The ingestion may be spontaneous (free ingestion), or may be compulsory (forced ingestion). That is, specifically, the administration step may be, for example, a step of supplying the active ingredient to the subject through blending with food/drink or feed, thereby allowing the subject to freely ingest the active ingredient. The administration may be oral administration or may be parenteral administration. The administration may be generally oral administration. The parenteral administration may include tube administration or rectal administration.

The administration mode of the active ingredient (for example, an administration target, an administration time, an administration period, an administration frequency, a dose, and other administration-related conditions) is not particularly limited as long as a desired effect such as a breast milk component enhancing effect may be obtained. The administration mode of the active ingredient may be properly set according to various conditions such as the type of the active ingredient, or the type, age, and health condition of the administration target.

The subject to which the active ingredient is administered is not particularly limited as long as a desired effect such as a breast milk component enhancing effect may be obtained. The subject to which the active ingredient is administered may include mammals. The mammal may include humans, cows, sheep, goats, buffaloes, reindeers, donkeys, camels, dogs, cats, pigs, and horses. Particularly, the mammal may include humans. The mammal may be male or may be female. Particularly, the mammal may be female. That is, more particularly, the mammal may include human females. At least in the case aimed at obtaining a breast milk-related effect such as a breast milk component enhancing effect, as for the subject to which the active ingredient is administered, those capable of producing breast milk (that is, female mammals) are selected.

For example, the active ingredient may be routinely administered, or may be administered during a specific period. For example, the active ingredient may be administered in advance during a period before the breast milk is produced, may be administered during a period in which the breast milk is being produced, or may be administered during these both periods. When the active ingredient is administered in advance during the period before the breast milk is produced, the breast milk component enhancing effect may be obtained during the subsequent period in which the breast milk is being produced. The specific period may include a pre-pregnancy period, a pregnancy period, a postpartum period, and a lactation period. Particularly, the specific period may include a pregnancy period, a postpartum period, and a lactation period. That is, in the case of humans, the subject to which the active ingredient is administered may include pregnant women or lactating women. The phrase "pregnant woman" refers to a human female going through a period from the beginning of pregnancy to 1 year after delivery. The phrase "lactating woman" refers to a human female who are breastfeeding. The administration of the active ingredient may be started before, for example, pregnancy, but it is preferable that the administration is performed during at least a pregnancy period, a postpartum period, or a lactation period. In the case of humans, specifically, the active ingredient may be administered during, for example, a period from the time before pregnancy until the end of lactation, a period from when pregnancy starts or is known until the end of lactation, a period from the $26^{th}$ week of pregnancy until the end of lactation, or a period from the $26^{th}$ week of pregnancy to 1 month after delivery. The active ingredient may be administered during the above described period when, for example, the breast milk-related effect such as a breast milk component enhancing effect is desired. Also, the active ingredient may be administered during the above described period except when, for example, the breast milk-related effect such as a breast milk component enhancing effect is desired. Also, the active ingredient may be administered during, for example, a period in which it is desired to obtain effects caused by administration of the active ingredient. Also, the active ingredient may be continuously administered during the entire period of the above-exemplified period, or may be administered only during a part of the period. The phrase "part of the period" may refer to, for example, a period of 10% or more, 20% or more, 30% or more, 50% or more, 70% or more, or 90% or more in regard to the entire period of the above-exemplified period. The active ingredient may be administered, for example, once a day, or may be administered in divided doses per day. Also, for example, the active ingredient may be administered daily, or may be administered once every several days or every several weeks. The dose of the active ingredient at each administration may or may not be the same.

The dose of the bacterium of the genus *Bifidobacterium* may be, for example, $2 \times 10^6$ cfu/kg/day or more, $2 \times 10^7$ cfu/kg/day or more, or $2 \times 10^8$ cfu/kg/day or more, may be $1 \times 10^{12}$ cfu/kg/day or less, $1 \times 10^{11}$ cfu/kg/day or less, $1 \times 10^{10}$ cfu/kg/day or less, or $1 \times 10^9$ cfu/kg/day or less, or may fall within the range of combinations thereof. In one aspect, the dose of the bacterium of the genus *Bifidobacterium* is preferably, for example, $2 \times 10^6$ cfu/kg/day to $1 \times 10^{12}$ cfu/kg/day, more preferably $2 \times 10^7$ cfu/kg/day to $1 \times 10^{11}$ cfu/kg/day, and further preferably $2 \times 10^8$ cfu/kg/day to $1 \times 10^{10}$ cfu/kg/day. Also, in one aspect, the dose of the bacterium of the genus *Bifidobacterium* is preferably, for example, $2 \times 10^6$ cfu/kg/day to $1 \times 10^{11}$ cfu/kg/day, more preferably $2 \times 10^7$ cfu/kg/day to $1 \times 10^{10}$ cfu/kg/day, and further preferably $2 \times 10^7$ cfu/kg/day to $1 \times 10^9$ cfu/kg/day. When the active ingredient is dead cells, "cfu" may be replaced with "cells." When two or more types of bacteria of the genus *Bifidobacterium* are used, the above-exemplified dose of the bacterium of the genus *Bifidobacterium* may be a total dose of these two or more types of bacteria of the genus *Bifidobacterium*, or may be each dose. That is, specifically, when as for the bacterium of the genus *Bifidobacterium*, *Bifidobacterium longum* and *Bifidobacterium breve* are used in combination, for example, the dose of each of the *Bifidobacterium longum* and the *Bifidobacterium breve* may fall within a range of the above exemplified dose of the bacterium of the genus *Bifidobacterium*.

Also, the dose of the prebiotic may be, for example, 0.02 g/kg/day or more, 0.05 g/kg/day or more, or 0.1 g/kg/day or more, may be 0.6 g/kg/day or less, 0.4 g/kg/day or less, or 0.2 g/kg/day or less, or may fall within the range of combinations thereof. The dose of the prebiotic is preferably, for example, 0.02 g/kg/day to 0.6 g/kg/day, and more preferably 0.05 g/kg/day to 0.4 g/kg/day. When two or more types of prebiotics are used, the above-exemplified dose of the prebiotic may be a total dose of these two or more types of prebiotics. Also, when a material containing prebiotic is used, unless otherwise specified, it is assumed that the dose of the prebiotic is calculated on the basis of the amount of the prebiotic itself in the corresponding material.

For example, the active ingredient may be administered to the subject, as it is, or may be prepared as a composition containing the active ingredient, such as a food/drink composition, a pharmaceutical composition, or a feed composition, and then administered to the subject. Regarding the composition containing the active ingredient, the description on the composition of the present invention may be applied correspondingly. When a plurality of active ingredients is used, the active ingredients may be administered to the subject in a previously mixed state, or may be administered to the subject separately. When the active ingredients are administered to the subject separately, the active ingredients may or may not be administered to the subject at the same time. When the active ingredients are not administered to the subject at the same time, the administration order of the active ingredients (for example, the order of administration of the bacterium of the genus *Bifidobacterium* and administration of the prebiotic) is not particularly limited. When the active ingredients are not administered to the subject at the same time, the interval between the administration of a part of the active ingredients and the administration of the rest of the active ingredients (for example, the interval between the administration of the bacterium of the genus *Bifidobacterium* and the administration of the prebiotic) is not particularly limited as long as a desired effect such as a breast milk component enhancing effect may be obtained. The interval between the administration of apart of the active ingredients and the administration of the rest of the active ingredients (for example, the interval between the administration of the bacterium of the genus *Bifidobacterium* and the administration of the prebiotic) may fall, for example, within 6 hours, within 3 hours, or within 1 hour. Also, the active ingredient may be administered alone or may be administered in combination with other ingredients. Other ingredients may include medicines or pharmaceutical compositions, foods or drinks or food/drink compositions, and feeds or feed compositions. These other ingredients may or may not be those to be used in the above-exemplified applications for enhancing the breast milk component or promoting CCL28 secretion.

The active ingredient may be administered to the subject by using, for example, the composition of the present invention (that is, by administering the composition of the present invention). That is, one aspect of the method of the present invention may be a method including a step of administering the composition of the present invention to the subject. The phrase "addition of the active ingredient" also includes addition of the composition of the present invention. The administration mode of the composition of the present invention (for example, an administration target, an administration time, an administration period, an administration frequency, a dose, and other administration-related conditions) is not particularly limited as long as a desired effect such as a breast milk component enhancing effect may be obtained. The administration mode of the composition of the present invention may be properly set according to various conditions such as the type or amount of the active ingredient, the types or amounts of other ingredients, the type or form (dosage form) of the composition, and the type, age, and health condition of the administration target. The description regarding the above-described administration mode of the active ingredient may be applied correspondingly when the composition of the present invention is administered to the subject. That is, the composition of the present invention may be administered to, for example, the above-exemplified subjects. Also, the dose of the composition of the present invention may be set such that, for example, the above-exemplified dose of the active ingredient may be obtained. Also, when a plurality of active ingredients is used, and when the active ingredients are separately included in the composition of the present invention, the active ingredients may be administered to the subject after being mixed with each other, or may be separately administered to the subject. Also, the composition of the present invention may be administered alone, or may be administered in combination with other ingredients such as medicines or pharmaceutical compositions, foods or drinks or food/drink compositions, and feeds or feed compositions.

The breast milk of the present invention may be obtained by the method of the present invention. Therefore, one aspect of the method of the present invention may be a method of producing the breast milk of the present invention. More specifically, one aspect of the method of the present invention may be a method of producing the breast milk of the present invention, which includes a step of administering the active ingredient to the subject, and a step of acquiring the breast milk of the present invention. The breast milk of the present invention may be acquired from the subject by, for example, a usual method used to collect breast milk, such as milking.

<4> Use of Breast Milk of the Present Invention

The breast milk of the present invention may be used by being administered to the subject. The breast milk of the present invention may be used so as to obtain, for example, the effect of the breast milk of the present invention.

For example, the breast milk of the present invention may be administered to the subject as it is, or after being properly subjected to treatments such as concentration, dilution, fractionation, heating, freezing, and drying. These treatments are not particularly limited as long as the effect of the breast milk of the present invention is not impaired. For example, in the case of fractionation, a fraction from which the effect of the breast milk of the present invention is obtained may be acquired and administered to the subject. Such a fraction may include fractions containing an enhanced breast milk component. Also, for example, the breast milk of the present invention may be prepared as a composition containing the breast milk of the present invention, such as a food/drink composition, a pharmaceutical composition, or a feed composition, and then administered to the subject. The composition containing the breast milk of the present invention may include the breast milk of the present invention, or may contain ingredients other than the breast milk of the present invention. The ingredients other than the breast milk of the present invention are not particularly limited as long as the effect of the breast milk of the present invention is not impaired. Also, the amount or the content ratio of each ingredient (that is, the breast milk of the present invention and optionally other ingredients) in the composition containing the breast milk of the present invention is not particularly limited as long as the effect of the breast milk of the present invention may be obtained. The amount or the content ratio of each ingredient in the composition containing the breast milk of the present invention may be properly set according to various conditions such as the type of the enhanced breast milk component, the types of other ingredients, the type, form (dosage form), and usage of the composition, and the type, age, and health condition of an administration target. Besides, regarding the composition containing the breast milk of the present invention, the description on the composition of the present invention may be applied correspondingly, except that, for example, the breast milk of the present invention is present instead of the above active ingredient, or in addition to the above active ingredient.

The subject to which the breast milk of the present invention is administered is not particularly limited. The subject to which the breast milk of the present invention is administered may include mammals. The mammal is the same as that described above. The subject to which the breast milk of the present invention is administered may be, for example, a mature individual, or may be an immature individual. Particularly, the subject to which the breast milk of the present invention is administered may be an immature individual. Specifically, the subject to which the breast milk of the present invention is administered may be an individual going through a period from birth to weaning. The subject to which the breast milk of the present invention is administered may include babies or infants in the case of humans. Particularly, the subject to which the breast milk of the present invention is administered may include babies in the case of humans. The phrase "baby" refers to a child under the age of 1 after birth. The phrase "infant" refers to a child over the age of 1 after birth before primary school attendance. Also, the subject to which the breast milk of the present invention is administered may include children under 7 years old, under 6 years old, under 5 years old, under 4 years old, under 3 years old, under 2 years old, or under 1 year old after birth, in the case of humans. The subject to which the breast milk of the present invention is administered may or may not be one belonging to the same species as the individual who produced the breast milk of the present invention (for example, the offspring of the corresponding individual). For example, the breast milk obtained from humans may be administered to humans. That is, specifically, for example, the method of the present invention may be carried out for a human, and the corresponding human may breastfeed an offspring so that the effect of the breast milk of the present invention may be obtained in the corresponding offspring. Also, for example, the breast milk obtained from mammals other than humans, such as cows, may be administered to humans.

The administration mode of the breast milk of the present invention (for example, a dose, an administration time, an administration period, an administration frequency, and other administration-related conditions) is not particularly limited as long as the effect of the breast milk of the present invention may be obtained. The administration mode of the breast milk of the present invention may be properly set according to various conditions such as the type of the enhanced breast milk component, or the type, age, and health condition of an administration target. The dose of the breast milk of the present invention may be set to, for example, an amount of milk normally ingested by the administration target. For example, the breast milk of the present invention may be routinely administered, or may be administered during a specific period. The specific period may include a period from birth to weaning. Besides, regarding the administration of the breast milk of the present invention, the description on the administration of the active ingredient in the method of the present invention may be applied correspondingly except that, for example, the breast milk of the present invention is administered instead of the above active ingredient, or in addition to the above active ingredient.

EXAMPLES

Hereinafter, the present invention will be described in more detail by using Examples, but the present invention is not limited to these Examples.

Example 1

Each of a *Bifidobacterium longum* BB536 strain (NITE BP-02621; hereinafter, also referred to as "BB536") and a *Bifidobacterium breve* M-16V strain (NITE BP-02622; hereinafter, also referred to as "M-16V") was anaerobically cultured for 12 h, at 37° C. in a culture medium of a MRS broth added with 0.05% cysteine hydrochloride. Microbial cells of both strains were collected, and suspended in sterilized PBS up to $5\times10^9$ cfu/ml in total, thereby preparing a microbial cell suspension (BB536+M-16V-containing PBS).

A 5% aqueous solution of fructooligosaccharides (FOS) (manufactured by Wako Pure Chemical Industries, Ltd.) was prepared, and was sterilized by filter filtration of 0.22 µm.

11-week-old germfree ICR mice (male and female) were purchased from Sankyo Lab Co., Ltd.

After acclimatization for 1 week, female mice (12-week-old) were divided into two groups (a synbiotics group and a germfree group). To the synbiotics group, 200 µl of the BB536+M-16V-containing PBS was orally administered (as the number of bacteria, $1\times10^9$ cfu each, $2\times10^9$ cfu in total), and after the administration, a sterilized 5% FOS solution was freely ingested so as to settle the administered bacteria. To the germfree group, the BB536+M-16V-containing PBS was not administered, and then, sterilized tap water was freely ingested. Mating was performed at 14 weeks of age, and then childbirth was performed. 14 days after the delivery, 1 I.U. oxytocin (manufactured by Sigma) was intraperitoneally administered, and 15 minutes later, milking was performed under isoflurane anesthesia. Then, a milk sample was obtained. Cells and lipids were removed from the obtained milk sample by centrifugation to obtain skim milk. The HSP70 (Heat Shock Protein 70) concentration, the IFN-γ concentration, the CCL8 concentration, and the CCL21 concentration in the obtained skim milk were measured by using an ELISA method or a multi-item simultaneous detector (Multiplex) (both are manufactured by R&D Systems).

Results are shown in Tables 1 to 4. In the synbiotics group, concentrations of HSP70, IFN-γ, CCL8, and CCL21 in the breast milk were increased as compared to those in the germfree group. That is, it became clear that the breast milk component may be enhanced by the use of the above bacteria in combination with the fructooligosaccharides.

TABLE 1

Concentration of HSP70 in skim milk on 14$^{th}$ day after delivery (ng/ml)

| | Average | Standard Error |
|---|---|---|
| Germfree Group | 4.78 | 0.95 |
| Synbiotics Group | 13.80 | 2.81 |

TABLE 2

Concentration of IFN-γ in skim milk on 14$^{th}$ day after delivery (pg/ml)

| | Average | Standard Error |
|---|---|---|
| Germfree Group | 7.12 | 1.58 |
| Synbiotics Group | 17.31 | 3.16 |

TABLE 3

Concentration of CCL8 in skim milk on 14$^{th}$ day after delivery (pg/ml)

| | Average | Standard Error |
|---|---|---|
| Germfree Group | 1208.37 | 139.13 |
| Synbiotics Group | 1977.62 | 215.93 |

TABLE 4

Concentration of CCL21 in skim milk on 14$^{th}$ day after delivery (pg/ml)

| | Average | Standard error |
|---|---|---|
| Germfree Group | 250.57 | 24.41 |
| Synbiotics Group | 352.61 | 24.95 |

Production Example 1

Each of a *Bifidobacterium breve* M-16V strain and a *Bifidobacterium longum* BB536 strain is inoculated into 3 mL of MRS liquid culture medium, and anaerobically cultured at 37° C. for 16 h. Then, the resultant culture solution is concentrated, and freeze-dried to obtain freeze-dried powder of the bacteria (bacterial powder). The bacterial powder is uniformly mixed with a whey protein concentrate (WPC) and fructooligosaccharides to obtain a composition. Twenty gram of the composition is dissolved in 200 g of water to obtain a composition that may be used for a specific use application, such as a composition for enhancing a breast milk component. The composition may be administered to a subject such as a pregnant woman or a lactating woman so as to obtain an effect such as an increase of the amount of the breast milk component.

Production Example 2

Each of a *Bifidobacterium breve* M-16V strain and a *Bifidobacterium longum* BB536 strain is inoculated into 3 mL of MRS liquid culture medium, and anaerobically cultured at 37° C. for 16 h. Then, the resultant culture solution is concentrated, and freeze-dried to obtain freeze-dried powder of the bacteria (bacterial powder). The bacterial powder is uniformly mixed with dry powder of a milk protein concentrate (MPC480, manufactured by Fonterra, protein content 80% by mass, casein protein:whey protein=about 8:2), and fructooligosaccharides to obtain a composition. Twenty gram of the composition is dissolved in 200 g of water to obtain a composition that may be used for a specific use application, such as a composition for enhancing a breast milk component. The composition may be administered to a subject such as a pregnant woman or a lactating woman so as to obtain an effect such as an increase of the amount of the breast milk component.

Production Example 3

Each of a *Bifidobacterium breve* M-16V strain and a *Bifidobacterium longum* BB536 strain is inoculated into 3 mL of MRS liquid culture medium, and anaerobically cultured at 37° C. for 16 h. Then, the resultant culture solution is concentrated, and freeze-dried to obtain freeze-dried powder of the bacteria (bacterial powder). Next, the bacterial powder, fructooligosaccharides, and crystalline cellulose are put into a stirring granulator and mixed. Then, granulation is performed with addition of purified water, and the resultant granulated product is dried. Then, a composition containing the bacteria, prebiotic, and an excipient, such as a composition for enhancing abreast milk component, is obtained, which has a granular form and may be used for a specific use application. The composition may be administered to a subject such as a pregnant woman or a lactating woman so as to obtain an effect such as an increase of the amount of the breast milk component.

Production Example 4

An example of a method for producing fermented milk in which a *Bifidobacterium breve* M-16V strain and a *Bifidobacterium longum* BB536 strain are added will be described below.

First, if necessary, a milk raw material is mixed with water or other components, and is preferably subjected to a homogenization treatment and a heat-sterilization treatment to obtain a sterilized milk preparation. The homogenization treatment and the heat-sterilization treatment may be performed by conventional methods.

Next, a lactic acid bacteria starter is added (inoculated) to the sterilized milk preparation, and fermentation is performed while a predetermined fermentation temperature is maintained. By the fermentation, curds are formed. As for the lactic acid bacteria starter, for example, lactic acid bacteria generally used for yogurt production, such as *Lactobacillus bulgaricus*, *Lactococcus lactis*, and *Streptococcus thermophilus*, may be used. When pH reaches a target value, the formed curds are crushed by stirring, and cooled to 10° C. or less to obtain fermented milk. By cooling to 10° C. or less, the activation of the lactic acid bacteria may be reduced, and the production of acid may be suppressed.

Then, the fermented milk is subjected to heat treatment to obtain heated fermented milk (heat-treated fermented milk). By properly heating the fermented milk, the activation of the lactic acid bacteria may be reduced, and the production of acid may be suppressed. Accordingly, during the subsequent production process and/or during storage of concentrated fermented milk containing Bifidobacteria and prebiotic, reduction of pH may be suppressed. As a result, the survival rate of the Bifidobacteria may be improved.

Next, a *Bifidobacterium breve* M-16V strain, a *Bifidobacterium longum* BB536 strain, and fructooligosaccharides are added to the heated fermented milk so as to obtain Bifidobacteria/prebiotic-containing fermented milk. The addition amount of each of the *Bifidobacterium breve* M-16V strain and the *Bifidobacterium longum* BB536 strain is preferably $1\times10^7$ to $1\times10^{11}$ CFU/ml, more preferably $1\times10^8$ to $1\times10^{10}$ CFU/ml with respect to the heated fermented milk.

Next, the Bifidobacteria/prebiotic-containing fermented milk is concentrated to obtain Bifidobacteria/prebiotic-containing concentrated fermented milk. The concentration may be performed by a conventionally known concentration method. The concentration method may include a centrifugal separation method or a membrane separation method. For example, in the centrifugal separation method, whey present in the concentration target (the Bifidobacteria/prebiotic-containing fermented milk) is removed to obtain the Bifidobacteria/prebiotic-containing concentrated fermented milk in which the solid content concentration is increased. The concentrated fermented milk obtained as described above may be ingested by a subject such as a pregnant woman or a lactating woman so as to obtain an effect such as an increase of the amount of the breast milk component.

Production Example 5

An example of a method for producing a powdered milk formula in which a *Bifidobacterium breve* M-16V strain and a *Bifidobacterium longum* BB536 strain are added will be described below.

Ten kilogram of desalted milk whey protein powder manufactured by Mirai, 6 kg of milk casein powder manufactured by Fonterra, 48 kg of lactose manufactured by Mirai, 920 g of a mineral mixture manufactured by Tomita Pharmaceutical Co., Ltd., 32 g of a vitamin mixture manufactured by Tanabe Seiyaku Co., Ltd., and prebiotics ingredients, that is, 900 g of fructooligosaccharides manufactured by Yakult Pharmaceutical Industry Co., Ltd., 500 g of lactulose manufactured by Morinaga Milk Industry Co., Ltd., 500 g of raffinose manufactured by Nippon Beet Sugar Manufacturing Co., Ltd., and 900 g of galactooligosaccharide liquid sugar manufactured by Yakult Pharmaceutical Industry Co., Ltd. are dissolved in 300 kg of warm water, and then dissolved at 90° C. for 10 min through heating, and homogenized with addition of 28 kg of prepared fat manufactured by Taiyo Yushi Corp. Then, sterilization and concentration steps are performed, and about 95 kg of oligosaccharide-blended powdered milk formula is prepared through spray-drying. To this, 100 g of bacterial powder (two strains, $1.8\times10^{11}$ cfu/g in total) (which is obtained when two strains (a *Bifidobacterium breve* M-16V strain and a *Bifidobacterium longum* BB536 strain) are added to 3 mL of MRS liquid culture medium, and anaerobically cultured at 37° C. for 16 h, and then the culture solution is concentrated, freeze-dried, and triturated with starch) is added to prepare about 95 kg of Bifidobacteria•oligosaccharide-blended powdered milk formula. When the Bifidobacteria• oligosaccharide-blended powdered milk formula is dissolved in water and becomes a milk preparation at a total solid content concentration of 14% (w/v) (as a standard milk preparation concentration), the number of Bifidobacteria of the two strains in the milk preparation becomes $2.7\times10^9$ cfu/100 ml in total. The Bifidobacteria•oligosaccharide-blended powdered milk formula obtained as described above may be ingested by a subject such as a pregnant woman or a lactating woman so as to obtain an effect such as an increase of the amount of the breast milk component.

Example 2

In this Example, when a lactating woman ingests a bacterium of the genus *Bifidobacterium*, the influence on CCL28 concentration in breast milk collected from the lactating woman was investigated.

<Target and Method>

Lactating women who have continuously daily ingested $5\times10^9$ to $1\times10^{10}$ *Bifidobacterium breve* M-16V strains (baby Bifidos, Morinaga Milk Industry Co., Ltd.; hereinafter, also referred to as "M-16V") during any two months in the period from $1^{st}$ month to 6th month after delivery were set as an ingestion group (n=11). Also, lactating women having no habits of M-16V ingestion were set as a control group (n=11). In the ingestion group, breast milk was collected the day before, two days before the M-16V ingestion start, and was designated as "$0^{th}$ month of ingestion." In the ingestion group, breast milk was further collected on the first month and the second month from the M-16V ingestion start. In the control group, after delivery, breast milk was collected at timings almost coincident with those in the case of the ingestion group. No significant difference was found in the subject background between the ingestion group and the control group (Table 5).

TABLE 5

| Subject Background | | | |
|---|---|---|---|
| | Breastfeeding days at $0^{th}$ month of ingestion (days after delivery) | Age at delivery (years old) | Gestational age (weeks) |
| Ingestion Group (n = 11) | 56.0 ± 32.0 | 33.8 ± 2.0 | 39.7 ± 0.9 |
| Control Group (n = 11) | 57.1 ± 30.7 | 31.1 ± 2.5 | 38.5 ± 0.9 |

※ regarding age and gestational age of control group, data on 9 out of 11.

The breast milk was centrifuged at 12,000 G, for 30 min, at 4° C., and whey other than a fat layer and precipitates was collected, and was used in measurement of CCL28. The measurement of CCL28 was carried out by using Human CCL28 DuoSet ELISA (R&D System) and DuoSet ELISA Ancillary Reagent Kit 2 (R&D System).

<Results>

Results are shown in FIG. 1. At the "$0^{th}$ month of ingestion," no difference was recognized in the CCL28 concentration between the ingestion group and the control group. Meanwhile, at the "$1^{st}$ month of ingestion" and the "$2^{nd}$ month of ingestion," the value of the CCL28 concentration in the ingestion group was significantly high as compared to that of the CCL28 concentration in the control group. Therefore, it was suggested that the CCL28 concentration in the breast milk is increased by ingestion of the bacterium of the genus *Bifidobacterium* such as M-16V.

Also, it is thought that an increase of the CCL28 concentration in the breast milk is caused by promotion of CCL28 secretion from mucosal epithelial cells present in a mammary gland. Here, mucosal epithelial cells secreting CCL28 are present not only in the mammary gland but also throughout the body. Therefore, it is thought that ingestion of the bacterium of the genus *Bifidobacterium* widely causes secretion promotion of CCL28 without limitation on CCL28 secretion promotion in the mammary gland.

Example 3

In this Example, when a lactating woman ingests a bacterium of the genus *Bifidobacterium*, the influence on Galectin-9 concentration in breast milk collected from the lactating woman was investigated.

<Target and Method>

Lactating women who have continuously daily ingested $5 \times 10^9$ to $1 \times 10^{10}$ *Bifidobacterium breve* M-16V strains (baby Bifidos, Morinaga Milk Industry Co., Ltd.; hereinafter, also referred to as "M-16V") during any two months in the period from 1st month to 6th month after delivery were set as an ingestion group (n=11). Also, lactating women having no habits of M-16V ingestion were set as a control group (n=11). In the ingestion group, breast milk was collected the day before, two days before the M-16V ingestion start, and was designated as "$0^{th}$ month of ingestion." In the ingestion group, breast milk was further collected on the first month and the second month from the M-16V ingestion start. Also, in the control group, after delivery, breast milk was collected at timings almost coincident with those in the case of the ingestion group. No significant difference was found in the subject background between the ingestion group and the control group (Table 6).

TABLE 6

| Subject Background | | | |
|---|---|---|---|
| | Breastfeeding days at $0^{th}$ month of ingestion (days after delivery) | Age at delivery (years old) | Gestational age (weeks) |
| Ingestion Group (n = 11) | 56.0 ± 32.0 | 33.8 ± 2.0 | 39.7 ± 0.9 |
| Control Group (n = 11) | 57.1 ± 30.7 | 31.1 ± 2.5 | 38.5 ± 0.9 |

※ regarding age and gestational age of control group, data on 9 out of 11.

The breast milk was centrifuged at 12,000 G, for 30 min, at 4° C., and whey other than a fat layer and precipitates was collected, and was used in measurement of Galectin-9. The measurement of Galectin-9 was carried out by using Human Magnetic Luminex Assay (R&D System). On the basis of the Galectin-9 concentration in the breast milk at the $0^{th}$ month of ingestion, change rates of the Galectin-9 concentration in the breast milk at the $1^{st}$ month and 2nd month of ingestion were calculated. The change rates were compared between groups of the ingestion group and the control group.

<Result>

Calculation results of change rates are shown in Table 7. Regarding the number of subjects in which the Galectin-9 concentration at the $2^{nd}$ month of ingestion was significantly higher than the Galectin-9 concentration at the $0^{th}$ month of ingestion (150% or more as the change rate), the ingestion group and the control group were compared by the $\chi 2$ test. The results are shown in Table 8. The number of subjects in which the Galectin-9 concentration was significantly increased (150% or more as the change rate) was significantly different between the ingestion group and the control group. Therefore, it was suggested that the Galectin-9 concentration in the breast milk is increased by ingestion of the bacterium of the genus *Bifidobacterium* such as M-16V.

TABLE 7

| | change rate on the basis of Galectin-9 concentration at $0^{th}$ month of ingestion | | | | | | | | | | |
|---|---|---|---|---|---|---|---|---|---|---|---|
| Ingestion group | S1 | S2 | S3 | S4 | S5 | S6 | S7 | S8 | S9 | S10 | S11 |
| $0^{th}$ month | 100% | 100% | 100% | 100% | 100% | 100% | 100% | 100% | 100% | 100% | 100% |
| $1^{th}$ month | 183% | 98% | 383% | 134% | 138% | 167% | — | 72% | — | 81% | 78% |
| $2^{th}$ month | 187% | 41% | 75% | 176% | 298% | 180% | 66% | 217% | 185% | 201% | 19% |
| Control Group | C1 | C2 | C3 | C4 | C5 | C6 | C7 | C8 | C9 | C10 | C11 |
| $0^{th}$ month | 100% | 100% | 100% | 100% | 100% | 100% | 100% | 100% | 100% | 100% | 100% |
| $1^{th}$ month | 69% | 71% | 70% | — | 94% | 48% | 12% | — | 88% | 163% | 199% |
| $2^{th}$ month | 122% | 95% | 84% | 101% | 89% | 91% | 17% | 94% | 41% | 199% | 167% |

TABLE 8

| $\chi 2$ test result | | | |
|---|---|---|---|
| | 150% or more | less than 150% | total |
| Ingestion Group | 7 | 4 | 11 |
| Control Group | 2 | 9 | 11 |
| Total | 9 | 13 | 22 |
| $\chi 2$ value | p value | | |
| 4.701 | 0.030 | | |

Production Example 6

A *Bifidobacterium breve* M-16V strain is inoculated into 3 mL of MRS liquid culture medium, and anaerobically cultured at 37° C. for 16 h. Then, the resultant culture solution is concentrated, and freeze-dried to obtain freeze-dried powder of the bacterium (bacterial powder). The bacterial powder is uniformly mixed with a whey protein concentrate (WPC) to obtain a composition. Twenty gram of the composition is dissolved in 200 g of water to obtain a composition that may be used for a specific use application, such as a composition for enhancing a breast milk component. The composition may be administered to a subject such as a pregnant woman or a lactating woman so as to obtain an effect such as an increase of the amount of the breast milk component.

Production Example 7

A *Bifidobacterium breve* M-16V strain is inoculated into 3 mL of MRS liquid culture medium, and anaerobically cultured at 37° C. for 16 h. Then, the resultant culture solution is concentrated, and freeze-dried to obtain freeze-dried powder of the bacterium (bacterial powder). The bacterial powder is uniformly mixed with dry powder of a milk protein concentrate (MPC480, manufactured by Fonterra, protein content 80% by mass, casein protein:whey protein=about 8:2) to obtain a composition. Twenty grams of the composition is dissolved in 200 g of water to obtain a composition that may be used for a specific use application, such as a composition for enhancing a breast milk component. The composition may be administered to a subject such as a pregnant woman or a lactating woman so as to obtain an effect such as an increase of the amount of the breast milk component.

Production Example 8

A *Bifidobacterium breve* M-16V strain is inoculated into 3 mL of MRS liquid culture medium, and anaerobically cultured at 37° C. for 16 h. Then, the resultant culture solution is concentrated, and freeze-dried to obtain freeze-dried powder of the bacterium (bacterial powder). Then, the bacterial powder and crystalline cellulose are put into a stirring granulator and mixed. Then, granulation is performed with addition of purified water, and the resultant granulated product is dried. Then, a composition containing the bacterium and an excipient, such as a composition for enhancing a breast milk component, is obtained, which has a granular form and may be used for a specific use application. The composition may be administered to a subject such as a pregnant woman or a lactating woman so as to obtain an effect such as an increase of the amount of the breast milk component.

Production Example 9

An example of a method for producing fermented milk in which a *Bifidobacterium breve* M-16V strain is added will be described below.

First, if necessary, a milk raw material is mixed with water or other components, and is preferably subjected to a homogenization treatment and a heat-sterilization treatment to obtain a sterilized milk preparation. The homogenization treatment and the heat-sterilization treatment may be performed by conventional methods.

Next, a lactic acid bacteria starter is added (inoculated) to the sterilized milk preparation, and fermentation is performed while a predetermined fermentation temperature is maintained. By the fermentation, curds are formed. As for the lactic acid bacteria starter, for example, lactic acid bacteria generally used for yogurt production, such as *Lactobacillus bulgaricus*, *Lactococcus lactis*, and *Streptococcus thermophilus*, may be used. When pH reaches a target value, the formed curds are crushed by stirring, and cooled to 10° C. or less to obtain fermented milk. By cooling to 10° C. or less, the activation of the lactic acid bacteria may be reduced, and the production of acid may be suppressed.

Then, the fermented milk is subjected to heat treatment to obtain heated fermented milk (heat-treated fermented milk). By properly heating the fermented milk, the activation of the lactic acid bacteria may be reduced and the production of acid may be suppressed. Accordingly, during the subsequent production process and/or during storage of concentrated fermented milk containing Bifidobacteria, reduction of pH may be suppressed. As a result, the survival rate of the Bifidobacteria may be improved.

Next, a *Bifidobacterium breve* M-16V strain is added to the heated fermented milk so as to obtain Bifidobacteria-containing fermented milk. The addition amount of the *Bifidobacterium breve* M-16V strain is preferably $1 \times 10^7$ to $1 \times 10^{11}$ CFU/ml, more preferably $1 \times 10^8$ to $1 \times 10^{10}$ CFU/ml with respect to the heated fermented milk.

Next, the Bifidobacteria-containing fermented milk is concentrated to obtain Bifidobacteria-containing concentrated fermented milk. The concentration may be performed by a conventionally known concentration method. The concentration method may include a centrifugal separation method or a membrane separation method. For example, in the centrifugal separation method, whey in the concentration target (the Bifidobacteria-containing fermented milk) is removed to obtain the Bifidobacteria-containing concentrated fermented milk in which the solid content concentration is increased. The concentrated fermented milk obtained as described above may be ingested by a subject such as a pregnant woman or a lactating woman so as to obtain an effect such as an increase of the amount of the breast milk component.

Production Example 10

An example of a method for producing a powdered milk formula in which a *Bifidobacterium breve* M-16V strain is added will be described below.

Ten kilogram of desalted milk whey protein powder manufactured by Mirai, 6 kg of milk casein powder manufactured by Fonterra, 48 kg of lactose manufactured by Mirai, 920 g of a mineral mixture manufactured by Tomita Pharmaceutical Co., Ltd., and 32 g of a vitamin mixture (manufactured by Tanabe Seiyaku Co., Ltd. are dissolved in 300 kg of warm water, and then dissolved at 90° C. for 10 min through heating, and homogenized with addition of 28 kg of prepared fat manufactured by Taiyo Yushi Corp. Then, sterilization and concentration steps are performed, and about 92 kg of powdered milk formula is prepared through spray-drying. To this, 100 g of bacterial powder ($0.9 \times 10^{11}$ cfu/g) (which is obtained when a *Bifidobacterium breve* M-16V strain is added to 3 mL of MRS liquid culture medium, and anaerobically cultured at 37° C. for 16 h, and the culture solution is concentrated, freeze-dried, and triturated with starch) is added to prepare about 92 kg of *Bifidobacterium*-blended powdered milk formula. When the *Bifidobacterium*-blended powdered milk formula is dissolved in water, and becomes a milk preparation at a total solid content concentration of 14% (w/v) (as a standard milk preparation concentration), the number of *Bifidobacterium* in the milk preparation becomes $1.35 \times 10^9$ cfu/100 ml. The *Bifidobacterium*-blended modified milk powder obtained as described above may be ingested by a subject such as a pregnant woman or a lactating woman so as to obtain an effect such as an increase of the amount of the breast milk component.

INDUSTRIAL APPLICABILITY

According to the present invention, it is possible to provide a composition that may be used for a specific use application, such as a composition for enhancing a breast milk component.

The invention claimed is:

1. A method of enhancing a breast milk component in a pregnant or lactating woman in need thereof, the method comprising a step of administering a composition comprising a therapeutically effective amount of *Bifidobacterium breve* to the woman; wherein the composition optionally further comprises a therapeutically effective amount of a bacterium of the species *Bifidobacterium longum*, wherein the breast milk component is selected from the group consisting of a heat-shock protein, a chemokine, an interferon, a lectin, and combinations thereof.

2. The method according to claim 1, wherein the breast milk component is selected from the group consisting of HSP70 (Heat Shock Protein 70), CCL8 (Chemokine Ligand 8), CCL21 (Chemokine Ligand 21), CCL28 (Chemokine Ligand 28), IFN-γ (Gamma-interferon), galectin 9, and combinations thereof.

3. The method according to claim 1, which further comprises a step of administering an effective amount of a prebiotic to the woman.

4. The method according to claim 3, wherein the prebiotic is an oligosaccharide.

5. The method according to claim 3, wherein the prebiotic is a fructooligosaccharide.

6. The method according to claim 1, wherein the *Bifidobacterium longum* is *Bifidobacterium longum* BB536 (NITE BP-02621).

7. The method according to claim 1, wherein the *Bifidobacterium breve* is *Bifidobacterium breve* M-16V (NITE BP-02622).

* * * * *